US008263585B2

(12) United States Patent
Bruce et al.

(10) Patent No.: US 8,263,585 B2
(45) Date of Patent: Sep. 11, 2012

(54) ORGANIC COMPOUNDS

(75) Inventors: Ian Bruce, Horsham (GB); Andrew Dunstan, Horsham (GB); Thomas Anthony Hunt, Horsham (GB); Catherine Howsham, Horsham (GB); Thomas Ullrich, Bottmingen (CH); Amarylla Horvath, Vienna (AT)

(73) Assignee: Novartis AG, Basel (CH)

( * ) Notice: Subject to any disclaimer, the term of this patent is extended or adjusted under 35 U.S.C. 154(b) by 1034 days.

(21) Appl. No.: 12/180,969

(22) Filed: Jul. 28, 2008

(65) Prior Publication Data

US 2009/0163463 A1 Jun. 25, 2009

(30) Foreign Application Priority Data

Jul. 26, 2007 (EP) .................................... 07113237

(51) Int. Cl.
*A61K 31/395* (2006.01)
*A61K 31/505* (2006.01)
*A61K 31/535* (2006.01)
*C07D 239/02* (2006.01)
*C07D 413/12* (2006.01)

(52) U.S. Cl. .................. 514/210.2; 514/235.8; 514/275; 544/122; 544/297

(58) Field of Classification Search ............... 514/210.2, 514/275, 235.8; 544/297, 122
See application file for complete search history.

(56) References Cited

U.S. PATENT DOCUMENTS

| 2005/0234101 A1 | 10/2005 | Stenkamp et al. |
| 2006/0030583 A1 | 2/2006 | Arnold et al. |
| 2009/0163463 A1 | 6/2009 | Bruce et al. |
| 2009/0239847 A1 | 9/2009 | Bruce et al. |

FOREIGN PATENT DOCUMENTS

| DE | 2 051 013 | 12/1971 |
| GB | 2 073 185 | 10/1981 |
| WO | WO 97/43267 | 11/1997 |
| WO | WO 01/46691 | 6/2001 |
| WO | WO 03/093297 | 11/2003 |
| WO | 2004/048365 | * 6/2004 |
| WO | WO 2004/048365 | 6/2004 |
| WO | WO 2004/076412 | 9/2004 |
| WO | WO 2004/085409 | 10/2004 |
| WO | WO 2006/021881 | 3/2006 |
| WO | WO 2006/021886 | 3/2006 |
| WO | WO 2006/051270 | 5/2006 |
| WO | WO 2007/095588 | 8/2007 |
| WO | WO 2008/012326 | 1/2008 |
| WO | WO 2008/038955 | 4/2008 |
| WO | WO 2008/053157 | 5/2008 |
| WO | WO 2008/094992 | 8/2008 |

OTHER PUBLICATIONS

Gregory Bennett et al., "Synthesis and Antiinflammatory Activity of Trisubstituted Pyrimidines and Triazines" *Journal Medicinal Chemistry* 21(7):623-628, 1978.
Nobuhiro Sato, "Studies on Pyrazines the Synthesis of 2-Hydroxy-6-phenylpyrazine and its Derivatives." *Journal of Heterocyclic Chemistry* 15(4):665-570, Jun. 1978.
Tokuhiro Watanabe et al., "A Convenient Synthesis of Methylamino and Dimethylamino Substituted Aromatic Compounds" *Synthesis* 1:39-41, Jan. 1980.
Katsunori TERANiSHI and Toshio Goto, "Synthesis and Chemiluminescence of Coelenterazine (Oploporus Luciferin) Analogues" *Bull Chem. Soc. Jpn.* 63(11):3132-3140, 1990.
Keith Jones et al., "A Suzuki Coupling Approach to Pyrazines Related to Coelenterazine" Synett 6:509-510, Jun. 1996.
Marine Keenan et al., "Highly Efficient and Flexible Total Synthesis of Coelenterazine" *Chem Commun.* pp. 323-324, 1997.
V. Craig Jordan, "Tamoxifen. A Most Unlikely Pioneering Medicine" *Nature Reviews: Drug Discovery* 2:205-213, 2003.
Sudha Vippagunta et al., "Crystalline Solids" *Advanced Drug Delivery Reviews* 48:3-26, 2001.
V. Hagen et al., "Potentiell Kardiotonika" *Pharmazieu* 47 (10):767-769, Jan. 2009.

* cited by examiner

*Primary Examiner* — James O Wilson
*Assistant Examiner* — Ebenezer O Sackey
(74) *Attorney, Agent, or Firm* — Mark W. Milstead

(57) ABSTRACT

The present invention concerns a compound of formula (I)

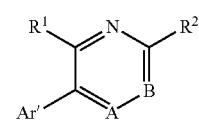

or a salt, suitably a pharmaceutically acceptable salt, or solvate thereof, wherein the groups $R^1$, $R^2$, Ar', A and B are defined in the description, to compositions and use of the compounds in the treatment of diseases ameliorated by inhibition of phosphatidylinositol 3-kinase.

9 Claims, No Drawings

ORGANIC COMPOUNDS

This application claims benefit under 35 U.S.C. §119(a)-(d) or (f) or 365(b) of European Patent Application No. 07113237.7, filed Jul. 26, 2007, the contents of which are incorporated herein by reference in their entirety.

The present invention relates to organic compounds, their preparation and their use as pharmaceuticals.

In a first aspect, the present invention provides compounds of formula I

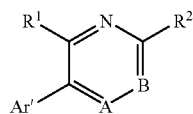

or a salt, suitably a pharmaceutically acceptable salt, or solvate thereof, wherein:
$R^1$ is hydrogen;
$R^2$ is hydrogen or amino;
A is $CR^3$;
B is $CR^{3a}$ or N;
Ar' is

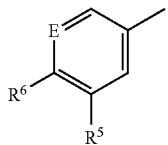

or an alternative $C_6$-$C_{14}$ aryl or 5-10 membered heteroaryl group, where each aryl or heteroaryl is optionally substituted by one or more substituents selected from List X;
E is CH or N;
$R^3$ and $R^{3a}$ are independently hydrogen, $C_1$-$C_6$-alkyl, $C_1$-$C_6$-haloalkyl, $C_4$-$C_8$ carbocyclyl, a 5-8 membered heterocyclyl or a group —Y—Z, where said rings are optionally substituted by one or more substituents selected from List X;
Y is a direct link, —O—$(CH_2)_n$— or —$N(R^4)$—$(CH_2)_o$—;
Z is phenyl or a 5-6 membered heteroaryl, where said rings are optionally substituted by one or more substituents selected from List X;
$R^4$ is hydrogen or $C_1$-$C_6$-alkyl;
$R^5$ is hydroxyl, $C_1$-$C_6$ alkyl, $C_1$-$C_6$ haloalkyl, $SO_2(C_1$-$C_6$ alkyl), $SO_2NR^7R^8$, $NR^9SO_2R^{10}$, $NR^{11}C(O)R^{12}$, $C(O)NR^{13}R^{14}$ or $NR^{15}R^{16}$;
$R^6$ is hydrogen, halo, hydroxyl, cyano, $C_1$-$C_3$-alkyl, $C_1$-$C_3$-haloalkyl, $C_1$-$C_3$-alkoxy or $C_1$-$C_3$-haloalkoxy; or $R^5$ and $R^6$ together form a 5-6 membered heteroaryl or 5-8 membered heterocyclyl, where each ring is optionally substituted by one or more substituents selected from List X;
$R^7$, $R^9$, $R^{11}$, $R^{13}$ and $R^{15}$ are independently hydrogen or $C_1$-$C_6$-alkyl;
$R^8$, $R^{10}$, $R^{12}$, $R^{14}$ and $R^{16}$ are independently hydrogen, $C_1$-$C_6$-alkyl or —$(CH_2)_p$—$R^{17}$, or $R^{10}$ and $R^{12}$ are additionally independently $C_1$-$C_6$-alkoxy, where said alkyl and alkoxy groups may be substituted by one to five halo or by hydroxyl, $C_1$-$C_6$-alkoxy, $NR^{11}R^{19}$ or CN;
$R^{17}$ is $C_6$-$C_{14}$-aryl, 5-10 membered heteroaryl, $C_4$-$C_8$ carbocyclyl, a 4-8 membered heterocyclyl, a $C_6$-$C_{14}$-aryl fused with a $C_4$-$C_8$ carbocyclyl or a 4-8 membered heterocyclyl, or a 5-10 membered heteroaryl fused with a $C_4$-$C_8$ carbocyclyl or a 4-8 membered heterocyclyl, where said rings are optionally substituted by one or more substituents selected from List X;
or $R^7$ and $R^8$, $R^{13}$ and $R^{14}$ or $R^{15}$ and $R^{16}$ may form a 4-8 membered heterocyclyl containing at least one N ring atom, where said ring is optionally substituted by halo, hydroxyl, $C_1$-$C_6$-alkyl, $C_1$-$C_6$-haloalkyl, $C_1$-$C_6$-alkoxy or $C_1$-$C_6$-haloalkoxy or cyano;
$R^{18}$ and $R^{19}$ are independently hydrogen or $C_1$-$C_6$-alkyl;
n is an integer from 0-2, o is an integer from 0-2 and p is an integer from 0-2;
List X is represented by hydroxyl, cyano, nitro, $C_6$-$C_6$-alkyl, $C_2$-$C_6$-alkenyl, $C_2$-$C_6$-alkynyl, $C_1$-$C_6$-alkoxy, $C_1$-$C_6$-alkenyloxy, $C_2$-$C_6$-alkynyloxy, —O—$(C_1$-$C_4$-alkylene)-$R^{20}$, —O—$(C_2$-$C_4$-alkylene)-$R^{21}$, halogen, $C_6$-$C_1$-alkylcarbonyl, carboxy, $C_1$-$C_6$-alkoxycarbonyl, amino, $C_1$-$C_6$-alkylamino, di-$C_1$-$C_6$-alkylamino, $C_1$-$C_6$-alkylaminocarbonyl, di-$C_1$-$C_6$-alkylaminocarbonyl, $C_1$-$C_6$-alkylcarbonylamino, $C_1$-$C_6$-alkylcarbonyl($C_1$-$C_6$-alkyl)amino, $C_1$-$C_6$-alkylsulfonylamino, $C_1$-$C_1$-alkylsulfonyl($C_6$-$C_6$-alkyl)amino, $C_1$-$C_6$-thioalkyl, $C_1$-$C_6$-alkylsulfinyl, $C_1$-$C_6$-alkylsufonyl, aminosulfonyl, $C_1$-$C_6$-alkylaminosulfonyl, di-$C_1$-$C_6$-alkylaminosulfonyl, phenyl or 5-6 membered heteroaryl, where each of the afore-mentioned hydrocarbon groups may be optionally substituted by one or more halogen, hydroxyl, $C_1$-$C_6$-alkoxy, amino, $C_1$-$C_6$-alkylamino, di-$C_1$-$C_6$-alkylamino or cyano, and where said phenyl or heteroaryl group may be optionally substituted by one or more groups selected from hydroxyl, cyano, nitro, $C_1$-$C_6$-alkyl, $C_1$-$C_6$-haloalkyl, $C_1$-$C_6$-alkenyl, $C_1$-$C_6$-alkynyl, $C_1$-$C_6$-alkoxy, $C_1$-$C_6$-alkenyloxy, $C_1$-$C_6$-alkynyloxy, halogen, $C_1$-$C_6$-alkylcarbonyl, carboxy, $C_1$-$C_6$-alkoxycarbonyl, amino, $C_1$-$C_6$-alkylamino, di-$C_1$-$C_6$-alkylamino, $C_1$-$C_6$-alkylaminocarbonyl, di-$C_1$-$C_6$-alkylaminocarbonyl, $C_1$-$C_6$-alkylcarbonylamino, $C_1$-$C_6$-alkylcarbonyl($C_1$-$C_6$-alkyl)amino, $C_1$-$C_6$-alkylsulfonylamino, $C_1$-$C_6$-alkylsulfonyl($C_1$-$C_6$-alkyl)amino, $C_1$-$C_6$-thioalkyl, $C_1$-$C_6$-alkylsulfinyl, $C_1$-$C_6$-alkylsulfonyl, aminosulfonyl, $C_1$-$C_6$-alkylaminosulfonyl or di-$C_1$-$C_6$-alkylaminosulfonyl groups;
$R^{20}$ represents $C_2$-$C_4$-alkenyl, $C_2$-$C_4$-alkynyl, halogen, cyano, nitro, $C_1$-$C_6$-alkylcarbonyl, carboxy, $C_1$-$C_6$-alkoxycarbonyl, $C_1$-$C_6$-thioalkyl, $C_1$-$C_6$-alkylsulfinyl, $C_1$-$C_6$-alkylsulfonyl, aminosulfonyl, $C_1$-$C_6$-alkylaminosulfonyl, di-$C_1$-$C_6$-alkylaminosulfonyl, phenyl, a C-linked 5-6 membered heteroaryl group, a $C_4$-$C_6$ carbocyclic group or a C-linked 5-6 nm membered heterocyclyl group, where said phenyl or cyclic groups may be optionally substituted by one or more hydroxyl, cyano, nitro, $C_1$-$C_6$-alkyl, $C_1$-$C_6$-alkenyl, $C_1$-$C_6$-alkynyl, $C_1$-$C_6$-alkoxy, $C_1$-$C_6$-alkenyloxy, $C_1$-$C_6$-alkynyloxy, halogen, $C_1$-$C_6$-alkylcarbonyl, carboxy, $C_1$-$C_6$-alkoxycarbonyl, amino, $C_1$-$C_6$-alkylamino, di-$C_1$-$C_6$-alkylamino, $C_1$-$C_6$-alkylaminocarbonyl, di-$C_1$-$C_6$-alkylaminocarbonyl, $C_1$-$C_6$-alkylcarbonylamino, $C_1$-$C_6$-alkylcarbonyl($C_1$-$C_6$-alkyl)amino, $C_1$-$C_6$-alkylsulfonylamino, $C_1$-$C_6$-alkylsulfonyl($C_1$-$C_6$-alkyl)amino, $C_1$-$C_6$-thioalkyl, $C_1$-$C_6$-alkylsulfinyl, $C_1$-$C_6$-alkylsulfonyl, aminosulfonyl, $C_1$-$C_6$-alkylaminosulfonyl or di-$C_1$-$C_6$-alkylaminosulfonyl groups, where each of the aforementioned hydrocarbon groups may be optionally substituted by one or more halogen, hydroxyl, $C_1$-$C_6$-alkoxy, amino, $C_1$-$C_6$-alkylamino, di-$C_1$-$C_6$-alkylamino or cyano; and
$R^{21}$ represents hydroxyl, $C_1$-$C_4$-alkoxy, $C_2$-$C_4$-alkenyloxy, $C_2$-$C_4$-alkynyloxy, amino, $C_1$-$C_6$-alkylamino, di-$C_1$-$C_6$-alkylamino, $C_1$-$C_6$-alkylaminocarbonyl, di-$C_1$-$C_6$-alkylaminocarbonyl, $C_1$-$C_6$-alkylcarbonylamino, $C_1$-$C_6$-alkylcarbonyl($C_1$-$C_6$-alkyl)amino, $C_1$-$C_6$alkylsulfonylamino, $C_1$-$C_6$-alkylsulfonyl($C_1$-$C_6$-alkyl)amino, an N-linked 5-6 membered heteroaryl group or an N-linked 5-6 membered heterocycyl where said cyclic groups may be optionally substituted by one or more hydroxyl, nitro, $C_1$-$C_6$-alkyl, $C_1$-$C_6$-alkenyl, $C_1$-$C_6$-alkynyl, $C_1$-$C_6$-alkoxy, $C_1$-$C_6$-alkenyloxy, $C_1$-$C_6$-alkynyloxy, halogen, $C_1$-$C_6$-alkylcarbonyl, carboxy, $C_1$-$C_6$-alkoxycarbonyl, amino, $C_1$-$C_6$-alkylamino, di-$C_1$-$C_6$-alkylamino, $C_1$-$C_6$-alkylaminocarbonyl, di-$C_1$-$C_6$-alkylaminocarbonyl, $C_1$-$C_6$-alkylcarbonylamino, $C_1$-$C_6$-alkylcarbonyl($C_1$-$C_6$-alkyl)amino, $C_1$-$C_6$-alkylsulfonylamino, $C_1$-$C_6$-alkylsulfonyl($C_1$-$C_6$-alkyl)amino, $C_1$-$C_6$-thioalkyl, $C_1$-$C_6$-alkylsulfinyl, $C_1$-$C_6$-alkylsulfonyl, aminosulfonyl, $C_1$-$C_6$-alkylaminosulfonyl or di-$C_1$-$C_6$-alkylaminosulfonyl groups, where each of the afore-mentioned hydrocarbon groups may be optionally substituted by one or more halogen, hydroxyl, $C_1$-$C_6$-alkoxy, amino, $C_1$-$C_6$-alkylamino, di-$C_1$-$C_6$-alkylamino or cyano.

Alkyl, alkenyl, alkynyl, alkylene, and alkoxy groups, containing the requisite number of carbon atoms, can be unbranched or branched. Examples of alkyl include methyl, ethyl, n-propyl, i-propyl, n-butyl, i-butyl, sec-butyl and t-butyl. Examples of alkoxy include methoxy, ethoxy, n-propoxy, i-propoxy, n-butoxy, i-butoxy, sec-butoxy and t-butoxy. Examples of alkylene include methylene, 1,1-ethylene, 1,2-ethylene, 1,1-propylene, 1,2-propylene, 1,3-propylene and 2,2-propylene.

"Halogen" or "halo" may be fluorine, chlorine, bromine or iodine.

Reference to a group optionally substituted refers to replacement of a C—H bond by the requisite bond. Where the substituent is a halogen, the group formed is defined as a haloalkyl group. For example, where the substituent is fluoro, common haloalkyl groups are trifluoroalkyl, 2,2,2-trifluoroethyl or 2,2,2,1,1-pentafluoroethyl groups.

$C_1$-$C_6$-haloalkyl refers to an alkyl group substituted by up to seven halogen groups, preferably fluoro groups. For example, where the substituent is fluoro, common haloalkyl groups are trifluoroalkyl, 2,2,2-trifluoroethyl or 2,2,2,1,1-pentafluoroethyl groups.

"Carbocyclic group" denotes a hydrocarbon ring having the requisite number of carbon atoms, for example cyclopropyl, cyclobutyl, cyclopentyl, cyclohexyl, cycloheptyl or cyclooctyl.

Reference to $C_6$-$C_{14}$ aryl refers to an aromatic carbocyclic group comprising one to three rings. Examples include phenyl, naphthyl, anthracyl and phenanthryl.

A heterocyclyl group refers to a saturated or partially unsaturated ring comprising one or more O, N or S heteroatoms. Specific examples of heterocyclyl groups include [1,3]dioxolane, [1,4]dioxane, oxiranyl, aziridinyl, oxetanyl, azetidinyl, tetrahydrofuranyl, pyrrolidinyl, tetrahydropyranyl, piperidinyl, morpholino, thiomorpholinyl, piperazinyl, azepinyl, oxazinyl, oxazepinyl and diazepinyl.

A heteroaryl group refers to an aromatic ring comprising one or more O, N or S heteroatoms. Examples of monocyclic heteroaryl groups include pyridyl, thienyl, furanyl, pyrrolyl, pyrazolyl, imidazoyl, oxazolyl, isoxazolyl, thiazolyl, isothiazolyl, triazolyl, oxadiazolyl, thiadiazolyl and tetrazolyl. Examples of bicyclic heteroaryl groups include indolyl, benzofuranyl, quinolyl, isoquinolyl and indazolyl.

Throughout this specification and in the claims that follow, unless the context requires otherwise, the word "comprise", or variations such as "comprises" or "comprising", will be understood to imply the inclusion of a stated integer or step or group of integers or steps but not the exclusion of any other integer or step or group of integers or steps.

The following suitable or preferred features of a compound of formula (I) may be incorporated into the definition of formula (I) and combined in any number of ways.

In one embodiment of formula (I), $R^2$ is amino. In another embodiment of formula (I), $R^2$ is hydrogen.

According to formula (I), where Ar' is an optionally substituted $C_6$-$C_{14}$ aryl, a subset of this group is represented by optionally substituted phenyl or naphthyl.

According to formula (I), where Ar' is a 5-10 membered heteroaryl, a subset of this group is represented by an optionally substituted thienyl or pyrimidyl, e.g. a 4-substituted pyrimidyl substituted by $C_1$-$C_6$-alkyl, e.g. tert-butyl.

According to formula (I), where Ar' is $C_6$-$C_{14}$ aryl or 6-10 membered heteroaryl group, substituted by one or more substituents selected from List X, a subset of List X substituents is represented by one to four, suitably one to two substituents independently selected from hydroxyl, $C_1$-$C_6$-alkyl, $C_1$-$C_6$-alkoxy, halogen, $C_1$-$C_6$-alkylcarbonyl, amino, $C_1$-$C_6$-alkylamino, di-$C_1$-$C_6$-alkylamino, $C_1$-$C_6$-alkylaminocarbonyl, di-$C_1$-$C_6$-alkylaminocarbonyl, $C_1$-$C_6$-alkylcarbonylamino, $C_1$-$C_6$-alkylcarbonyl($C_1$-$C_6$-alkyl)amino, $C_1$-$C_6$-alkylsulfonylamino, $C_1$-$C_6$-alkylsulfonyl($C_1$-$C_6$-alkyl)amino, $C_1$-$C_6$-alkylsulfinyl, $C_1$-$C_6$-alkylsulfonyl, aminosulfonyl, $C_1$-$C_6$-alkylaminosulfonyl or di-$C_1$-$C_6$-alkylaminosulfonyl, where each of the afore-mentioned hydrocarbon groups may be optionally substituted by one or more, suitably one to three, more suitably one, halogen, hydroxyl, $C_1$-$C_6$-alkoxy, amino, $C_1$-$C_6$-alkylamino, di-$C_1$-$C_6$-alkylamino or cyano.

According to formula (I), Ar' is suitably an optionally substituted pyrimidyl, e.g. 4-substituted pyrimidyl substituted by $C_1$-$C_6$-alkyl, e.g. tert-butyl, or Ar' is suitably

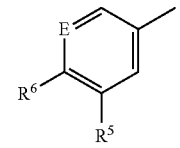

According to formula (I), Ar' is preferably

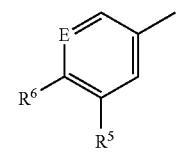

According to formula (I), where $R^3$ is a group optionally substituted by List X, a subset of List X substituents is represented by one or more, suitably one or two groups independently selected from hydroxyl, cyano, $C_1$-$C_6$-alkyl, $C_1$-$C_6$-alkoxy, halogen, $C_1$-$C_6$-alkylcarbonyl, amino, $C_1$-$C_6$-alkylamino, di-$C_1$-$C_6$-alkylamino, $C_1$-$C_6$-alkylaminocarbonyl, di-$C_1$-$C_6$-alkylaminocarbonyl, $C_1$-$C_6$-alkylcarbonylamino, $C_1$-$C_6$-alkylcarbonyl($C_1$-$C_6$-alkyl)amino, where each of the afore-mentioned hydrocarbon groups may be optionally substituted by one or more halogen, hydroxyl and $C_1$-$C_6$-alkoxy, suitably halo, e.g. fluoro.

According to formula (I), $R^3$ is suitably
(i) hydrogen,
(ii) $C_1$-$C_6$-alkyl, e.g. methyl,
(iii) a 5-8 membered heterocyclyl, e.g. N-piperidyl, optionally substituted, e.g. by hydroxyl or fluoro, e.g. 4-hydroxy or 4-fluoro or N-morpholinyl, (iv) phenoxy, optionally substituted, e.g. by one or more halogen, e.g. fluoro and chloro,
(v) benzyloxy, optionally substituted, e.g. by one or more halogen, e.g. fluoro and chloro,
(vi) 5-6 membered heteroaryloxy, e.g. pyridyloxy,
(vii) 5-6 membered heteroarylmethoxy, e.g. pyridylmethoxy,
(viii) N-anilino, optionally substituted, e.g. by one or more halogen, e.g. fluoro or chloro, or
(ix) benzylamino, optionally substituted, e.g. by one or more halogen, e.g. chloro.

According to formula (I), A is preferably CH or CMe.
According to formula (I), B is preferably N.
According to formula (I), in one embodiment, F is CH. In another embodiment of formula (I), E is N.
According to formula (I), where $R^5$ and $R^6$ form a ring, a subset of the Ar' rings formed is represented by an optionally substituted naphthyl or indolyl, e.g. 5-indolyl.
According to formula (I), $R^5$ is suitably $C_1$-$C_3$ haloalkyl, e.g. trifluoromethyl, $NR^{15}R^{16}$, e.g. benzylamino, $SO_2NR^7R^8$ or $NR^9SO_2R^{10}$, more suitably $SO_2NR^7R^8$ or $NR^9SO_2R^{10}$.
According to formula (I), when $R^5$ is $NR^{15}R^{16}$, $R^{15}$ is suitably hydrogen and $R^{16}$ is suitably benzyl.
Where $R^7$ and $R^8$ form a 4-8 membered heterocycyl ring containing at least one N and optionally one O or S, the ring is suitably morpholino, e.g. 4-morpholino, azetidyl, optionally substituted, e.g. by hydroxyl, pyrrolidyl, piperidyl, optionally substituted, e.g. by hydroxyl, e.g. 4-hydroxyl, or piperazinyl, optionally substituted by $C_1$-$C_6$-alkyl, e.g. methyl, ethyl or isopropyl, e.g. 4-methylpiperazinyl, 4-ethylpiperazinyl or 4-isopropylpiperazinyl.
According to formula (I), $R^7$ is suitably hydrogen or methyl, preferably hydrogen.
According to formula (I), where $R^8$ is $(CH_2)_p$—$R^{17}$ and p is 0, $R^{17}$ is suitably optionally substituted or fused phenyl, e.g. benzo[1,3]dioxole; 5-6 membered heteroaryl, e.g. pyridyl (such as 3-pyridyl); $C_4$-$C_8$-carbocyclyl, e.g. cyclopentyl, cyclohexyl or cycloheptyl; or 5-8 membered heterocyclyl, e.g. tetrahydropyran. Where $R^8$ is $(CH_2)_p$—$R^{17}$ and p is 1, $R^{17}$ is suitably optionally substituted phenyl. Where $R^9$ is $(CH_2)_p$—$R^{17}$ and p is 2, $R^{17}$ is suitably a 5-8 membered heterocyclyl, e.g. morpholino.
According to formula (I), $R^8$ is suitably $C_1$-$C_6$-alkyl, e.g. methyl or n-propyl; $C_1$-$C_6$-alkoxy-$C_1$-$C_6$-alkyl, e.g. 2-methoxyethyl; hydroxy$C_1$-$C_6$-alkyl, e.g. 2-hydroxyethyl; cyano$C_1$-$C_6$-alkyl, e.g. 2-cyanoethyl; $NR^{18}R^{19}$—$C_1$-$C_6$-alkyl, e.g. 2-dimethylaminoethyl; optionally substituted phenyl; fused phenyl, e.g. benzo[1,3]dioxole; 5-6 membered heteroaryl, e.g. pyridyl (such as 3-pyridyl); $C_4$-$C_8$-carbocyclyl, e.g. cyclopentyl, cyclohexyl or cycloheptyl; 5-8 membered heterocyclyl, e.g. tetrahydropyran; optionally substituted benzyl; or 5-8 membered heterocyclylethyl, e.g. morpholinoethyl. Preferably $R^8$ is cyclohexyl. Also preferably, $R^8$ is optionally substituted or fused phenyl.
According to formula (I), where $R^8$ is phenyl substituted or optionally substituted by List X, a subset of List X substituents is represented by one or more, suitably one or two groups independently selected from hydroxyl, cyano, $C_1$-$C_6$-alkyl, $C_1$-$C_6$-alkoxy, halogen, $C_1$-$C_6$-alkylcarbonyl, amino, $C_1$-$C_6$-alkylamino, di-$C_1$-$C_6$-alkylamino, $C_1$-$C_6$-alkylaminocarbonyl, di-$C_1$-$C_6$-alkylaminocarbonyl, $C_1$-$C_6$-alkylcarbonylamino, $C_1$-$C_6$-alkylcarbonyl($C_1$-$C_6$-alkyl)amino or 5-6 membered heteroaryl, where each of the afore-mentioned hydrocarbon groups may be optionally substituted by one or more halogen, hydroxyl and $C_1$-$C_6$-alkoxy. Suitably, the phenyl substituents are selected from one or more cyano, trifluoromethyl, $C_1$-$C_6$-alkyl, e.g. methyl, halo, e.g. fluoro or chloro and 5-6 membered heteroaryl, e.g. imidazolyl. Preferably, the phenyl substituents are selected from 3-cyano, 3-trifluoromethyl, 3-methyl-4-fluoro, 4-chloro, 3,4-dichloro and 3-imidazolyl.

According to formula (I), $R^9$ is suitably hydrogen or methyl, preferably hydrogen.
According to formula (I), $R^{10}$ is suitably $C_1$-$C_6$-alkyl, e.g. methyl, n-propyl, $C_1$-$C_6$-alkoxy-$C_1$-$C_6$-alkyl, e.g. 2-methoxyethyl, hydroxyC1-$C_6$-alkyl, e.g. 2-hydroxyethyl, cyano$C_1$-$C_6$-alkyl, e.g. 2-cyanoethyl, $NR^{18}R^{19}$—$C_1$-$C_6$-alkyl, e.g. 2-dimethylaminoethyl, optionally substituted phenyl or a 5-6 membered heteroaryl, e.g. pyridyl, e.g. 3-pyridyl.
According to formula (I), when $R^5$ is $NR^9SO_2R^{10}$, $R^9$ is suitably hydrogen and $R^{10}$ is suitably optionally substituted phenyl or $C_1$-$C_6$-alkyl, e.g. methyl.
According to formula (I), where $R^{10}$ is phenyl optionally substituted by List X, a subset of List X substituents is represented by one or more, suitably one or two groups independently selected from hydroxyl, cyano, $C_1$-$C_6$-alkyl, $C_1$-$C_6$-alkoxy, halogen, $C_1$-$C_6$-alkylcarbonyl, amino, $C_1$-$C_6$-alkylamino, di-$C_1$-$C_6$-alkylamino, $C_1$-$C_6$-alkylaminocarbonyl, di-$C_1$-$C_6$-alkylaminocarbonyl, $C_1$-$C_6$-alkylcarbonylamino, $C_1$-$C_6$-alkylcarbonyl($C_1$-$C_6$-alkyl)amino, where each of the afore-mentioned hydrocarbon groups may be optionally substituted by one or more halogen, hydroxyl and $C_1$-$C_6$-alkoxy.
According to formula (I), where $R^5$ and $R^6$ form a ring optionally substituted by List X, a subset of List X substituents is represented by one or more, suitably one or two groups independently selected from hydroxyl, cyano, $C_1$-$C_6$-alkyl, $C_1$-$C_6$-alkoxy, halogen, $C_1$-$C_6$-alkylcarbonyl, amino, $C_1$-$C_6$-alkylamino, di-$C_1$-$C_6$-alkylamino, $C_1$-$C_6$-alkylaminocarbonyl, di-$C_1$-$C_6$-alkylaminocarbonyl, $C_1$-$C_6$-alkylcarbonylamino, $C_1$-$C_6$-alkylcarbonyl($C_1$-$C_6$-alkyl)amino, where each of the afore-mentioned hydrocarbon groups may be optionally substituted by one or more halogen, hydroxyl and $C_1$-$C_6$-alkoxy.
According to formula (I), $R^6$ is suitably halo, e.g. fluoro, bromo or chloro, $C_1$-$C_3$-alkyl, e.g. methyl or $C_1$-$C_3$-alkoxy, e.g. methoxy. Preferably, $R^6$ is chloro.
According to formula (I), a suitable sub-formula of the compounds of the present invention is defined by formula (Ia)

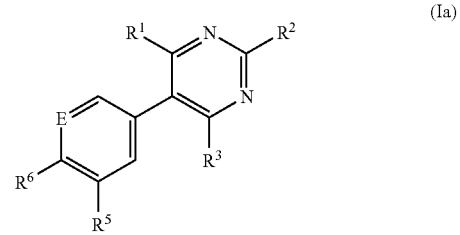

(Ia)

or a salt, suitably a pharmaceutically acceptable salt, or solvate thereof, wherein: $R^1$ is hydrogen; $R^2$ is hydrogen or amino; $R^3$ is hydrogen or methyl; E is CH or N; $R^5$ is $SO_2NR^7R^8$ or $NR^9SO_2R^{10}$, $R^6$ is halo or $C_1$-$C_3$-alkyl; $R^7$ and $R^9$ are independently hydrogen or methyl; $R^8$ and $R^{10}$ are the group —$(CH_2)_p$—$R^{17}$, where said alkyl groups may be substituted by one to five halo or by hydroxyl, $C_1$-$C_6$-alkoxy, $NR^{18}R^{19}$ or CN; or $R^7$ and $R^8$ form a 4-8 membered heterocyclyl containing at least one N ring atom, where said rings are optionally substituted by one or more halo, hydroxyl, cyano or $C_1$-$C_6$-alkyl; $R^{17}$ is $C_1$-$C_6$-alkyl, optionally substituted phenyl, 5-6 membered heteroaryl, $C_4$-$C_8$-carbocyclyl or 5-8 membered heterocyclyl; where said rings are optionally substituted by one or more hydroxyl, cyano, $C_1$-$C_6$-alkyl, $C_1$-$C_6$-alkoxy, halogen, $C_1$-$C_6$-alkylcarbonyl, amino, $C_1$-$C_6$-alkylamino, di-$C_1$-$C_6$-alkylamino, $C_1$-$C_6$-alkylaminocarbonyl, di-$C_1$-$C_6$-alkylaminocarbonyl, $C_1$-$C_6$-alkylcarbonylamino, $C_1$-$C_6$-alkylcarbonyl($C_1$-$C_6$-alkyl)amino or 5-6 membered heteroaryl, where each of the afore-mentioned hydrocarbon groups may be optionally substituted by one or more halogen, hydroxyl and $C_1$-$C_6$-alkoxy;

$R^{18}$ and $R^{19}$ are independently hydrogen or $C_1$-$C_6$-alkyl; and p is an integer from 0-2.

Suitably, $R^1$ is hydrogen, $R^2$ is amino, $R^3$ is methyl and E is CH.

A suitable individual compound of the invention is selected from:

5-(2-Amino-4-methyl-pyrimidin-5-yl)-2-chloro-N-phenyl-benzenesulfonamide;
5-(2-Amino-4-methyl-pyrimidin-5-yl)-2-bromo-N-(2-hydroxy-ethyl)-benzenesulfonamide;
5-(2-Amino-4-methyl-pyrimidin-5-yl)-2-bromo-N-propyl-benzenesulfonamide;
5-(2-Amino-4-methyl-pyrimidin-5-yl)-2-bromo-N-(2-hydroxy-ethyl)-N-methyl-benzenesulfonamide;
5-(2-Amino-4-methyl-pyrimidin-5-yl)-2-chloro-N-methyl-benzenesulfonamide;
5-(2-Amino-4-methyl-pyrimidin-5-yl)-2-methyl-N-phenyl-benzenesulfonamide
5-(2-Amino-4-methyl-pyrimidin-5-yl)-2-fluoro-N-phenyl-benzenesulfonamide;
5-(2-Amino-4-methyl-pyrimidin-5-yl)-2-bromo-N-(2-methoxy-ethyl)-N-methyl-benzenesulfonamide;
5-(2-Amino-4-methyl-pyrimidin-5-yl)-2-chloro-N-(2-hydroxy-ethyl)-N-methyl-benzenesulfonamide;
5-(2-Amino-4-methyl-pyrimidin-5-yl)-2-bromo-N-(2-methoxy-ethyl)-benzenesulfonamide;
5-(2-Amino-4-methyl-pyrimidin-5-yl)-2-chloro-N-(2-methoxy-ethyl)-benzenesulfonamide;
5-[4-Chloro-3-(pyrrolidine-1-sulfonyl)-phenyl]-4-methyl-pyrimidin-2-ylamine;
5-(2-Amino-4-methyl-pyrimidin-5-yl)-N-(2-hydroxy-ethyl)-2-methoxy-benzenesulfonamide;
5-[4-Bromo-3-(pyrrolidine-1-sulfonyl)-phenyl]-4-methyl-pyrimidin-2-ylamine;
5-(2-Amino-4-methyl-pyrimidin-5-yl)-2-chloro-N,N-dimethyl-benzenesulfonamide;
5-(2-Amino-4-methyl-pyrimidin-5-yl)-2-chloro-N-(2-methoxy-ethyl)-N-methyl-benzenesulfonamide;
5-(2-Amino-4-methyl-pyrimidin-5-yl)-N-(2-hydroxy-ethyl)-2-methyl-benzenesulfonamide;
5-[4-Bromo-3-(morpholine-4-sulfonyl)-phenyl]-4-methyl-pyrimidin-2-ylamine;
5-[4-Bromo-3-(4-methyl-piperazine-1-sulfonyl)-phenyl]-4-methyl-pyrimidin-2-ylamine;
5-(2-Amino-4-methyl-pyrimidin-5-yl)-2-bromo-N-(2-dimethylamino-ethyl)-benzenesulfonamide;
5-(2-Amino-4-methyl-pyrimidin-5-yl)-2,N,N-trimethyl-benzenesulfonamide;
5-(2-Amino-4-methyl-pyrimidin-5-yl)-N-(2-cyano-ethyl)-2-methyl-benzenesulfonamide;
5-[4-Chloro-3-(morpholine-4-sulfonyl)-phenyl]-4-methyl-pyrimidin-2-ylamine;
5-(2-Amino-4-methyl-pyrimidin-5-yl)-2-fluoro-N-propyl-benzenesulfonamide;
5-(2-Amino-4-methyl-pyrimidin-5-yl)-N-(2-cyano-ethyl)-2-fluoro-benzenesulfonamide;
5-(2-Amino-4-methyl-pyrimidin-5-yl)-N-benzyl-2-methyl-benzenesulfonamide;
5-[4-Chloro-3-(4-methyl-piperazine-1-sulfonyl)-phenyl]-4-methyl-pyrimidin-2-ylamine;
5-(2-Amino-4-methyl-pyrimidin-5-yl)-2-fluoro-N-(2-methoxy-ethyl)-N-methyl-benzenesulfonamide;
5-(2-Amino-4-methyl-pyrimidin-5-yl)-2-chloro-N-(2-hydroxy-ethyl)-benzenesulfonamide;
1-[5-(2-Amino-4-methyl-pyrimidin-5-yl)-2-chloro-benzenesulfonyl]-azetidin-3-ol;
5-(2-Amino-4-methyl-pyrimidin-5-yl)-2-bromo-N,N-dimethyl-benzenesulfonamide;
5-[4-Chloro-3-(4-ethyl-piperazine-1-sulfonyl)-phenyl]-4-methyl-pyrimidin-2-ylamine;
5-[4-Chloro-3-(4-isopropyl-piperazine-1-sulfonyl)-phenyl]-4-methyl-pyrimidin-2-ylamine;
5-(2-Amino-4-methyl-pyrimidin-5-yl)-2-chloro-N-cyclohexyl-benzenesulfonamide;
5-(2-Amino-4-methyl-pyrimidin-5-yl)-2-chloro-N-(2-cyano-ethyl)-benzenesulfonamide;
5-(2-Amino-4-methyl-pyrimidin-5-yl)-2-chloro-N-cyclopentyl-benzenesulfonamide;
5-(2-Amino-4-methyl-pyrimidin-5-yl)-2-chloro-N-(2-morpholin-4-yl-ethyl)-benzenesulfonamide;
5-(2-Amino-4-methyl-pyrimidin-5-yl)-N-benzyl-2-chloro-benzenesulfonamide;
5-(2-Amino-4-methyl-pyrimidin-5-yl)-2-chloro-N-(3-cyano-phenyl)-benzenesulfonamide;
5-(2-Amino-4-methyl-pyrimidin-5-yl)-2-chloro-N-methyl-N-(3-trifluoromethyl-phenyl)-benzenesulfonamide;
5-(2-Amino-4-methyl-pyrimidin-5-yl)-2-chloro-N-(4-fluoro-3-methyl-phenyl)-benzenesulfonamide;
5-(2-Amino-4-methyl-pyrimidin-5-yl)-2-chloro-N-(3-trifluoromethyl-phenyl)-benzenesulfonamide;
5-(2-Amino-4-methyl-pyrimidin-5-yl)-2-chloro-N-(4-chloro-phenyl)-benzenesulfonamide;
5-(2-Amino-4-methyl-pyrimidin-5-yl)-2-chloro-N-(4-chloro-phenyl)-N-methyl-benzenesulfonamide;
5-(2-Amino-4-methyl-pyrimidin-5-yl)-2-chloro-N-(3,4-dichloro-phenyl)-N-methyl-benzenesulfonamide;
5-(2-Amino-4-methyl-pyrimidin-5-yl)-2-chloro-N-methyl-N-phenyl-benzenesulfonamide;
5-(2-Amino-4-methyl-pyrimidin-5-yl)-N-benzo[1,3]dioxol-5-yl-2-chloro-N-methyl-benzenesulfonamide;
5-(2-Amino-4-methyl-pyrimidin-5-yl)-2-chloro-N-(3-imidazol-1-yl-phenyl)-benzenesulfonamide;
N-[5-(2-Amino-4-methyl-pyrimidin-5-yl)-2-chloro-phenyl]-methanesulfonamide;
N-[5-(2-Amino-4-methyl-pyrimidin-5-yl)-2-chloro-phenyl]-benzenesulfonamide;
5-(2-Amino-4-methyl-pyrimidin-5-yl)-2-chloro-N-(tetrahydro-pyran-4-yl)-benzenesulfonamide;
5-(2-Amino-4-methyl-pyrimidin-5-yl)-2-chloro-N-cycloheptyl-benzenesulfonamide;
1-[5-(2-Amino-4-methyl-pyrimidin-5-yl)-2-chloro-benzenesulfonyl]-piperidin-4-ol;
5-(2-Amino-4-methyl-pyrimidin-5-yl)-N-benzo[1,3]dioxol-5-yl-2-chloro-benzenesulfonamide;
5-(2-Amino-4-methyl-pyrimidin-5-yl)-2-chloro-N-pyridin-3-yl-benzenesulfonamide;
2-tert-Butyl-4'-methyl-[4,5']bipyrimidinyl-2'-ylamine;
5-(2-Amino-4-methyl-pyrimidin-5-yl)-2-chloro-N-cyclopropyl-benzenesulfonamide;
5-(2-Amino-4-methyl-pyrimidin-5-yl)-2-chloro-N-cyclobutyl-benzenesulfonamide;
5-[3-(Azetidine-1-sulfonyl)-4-chloro-phenyl]-4-methyl-pyrimidin-2-ylamine;
5-(2-Amino-4-methyl-pyrimidin-5-yl)-N-bicyclo[3.2.1]oct-3-yl-2-chloro-benzenesulfonamide;

5-(2-Amino-4-methyl-pyrimidin-5-yl)-2-chloro-N-((1R,2R)-2-hydroxy-cyclohexyl) benzenesulfonamide;
5-(2-Amino-4-methyl-pyrimidin-5-yl)-2-chloro-N-(4,4-difluoro-cyclohexyl)-benzenesulfonamide;
5-(2-Amino-4-methyl-pyrimidin-5-yl)-2-chloro-N-(5-hydroxy-adamantan-2-yl)-benzenesulfonamide;
5-(2-Amino-4-methyl-pyrimidin-5-yl)-2-chloro-N-(3-hydroxy-adamantan-1-yl)-benzenesulfonamide;
5-(2-Amino-4-methyl-pyrimidin-5-yl)-2-chloro-N-(2,2-dimethyl-propyl)-benzenesulfonamide;
5-(2-Amino-4-methyl-pyrimidin-5-yl)-2-chloro-N-(2-pyridin-4-yl-ethyl)-benzenesulfonamide;
5-(2-Amino-4-methyl-pyrimidin-5-yl)-2-chloro-N-(3-pyridin-3-yl-propyl)-benzenesulfonamide;
5-(2-Amino-4-methyl-pyrimidin-5-yl)-2-chloro-N-(4-pyridin-3-yl-butyl)-benzenesulfonamide;
5-(2-Amino-4-methyl-pyrimidin-5-yl)-N-pyridin-2-yl-2-chloro-benzenesulfonamide;
5-(2-Amino-4-methyl-pyrimidin-5-yl)-N-pyridin-4-yl-2-chloro-benzenesulfonamide;
trans-{4-[5-(2-Amino-4-methyl-pyrimidin-5-yl)-2-chloro-benzenesulfonylamino]-cyclohexylmethyl}-carbamic acid tert-butyl ester;
trans-{4-[5-(2-Amino-4-methyl-pyrimidin-5-yl)-2-chloro-benzenesulfonylamino]-cyclohexyl}-carbamic acid tert-butyl ester;
cis-{4-[5-(2-Amino-4-methyl-pyrimidin-5-yl)-2-chloro-benzenesulfonylamino]-cyclohexyl}-carbamic acid tert-butyl ester;
N-(4-Aminomethyl-cyclohexyl)-5-(2-amino-4-methyl-pyrimidin-5-yl)-2-chloro-benzenesulfonamide;
5-(2-Amino-4-methyl-pyrimidin-5-yl)-2-chloro-N-piperidin-4-yl-benzenesulfonamide;
trans-N-(4-Amino-cyclohexyl)-5-(2-amino-4-methyl-pyrimidin-5-yl)-2-chloro-benzenesulfonamide;
cis-N-(4-Amino-cyclohexyl)-5-(2-amino-4-methyl-piperidin-5-yl)-2-chloro-benzenesulfonamide;
N-{4-[5-(2-Amino-4-methyl-pyrimidin-5-yl)-2-chloro-benzenesulfonylamino]-cyclohexylmethyl}-acetamide;
N-(1-Acetyl-piperidin-4-yl)-5-(2-amino-4-methyl-pyrimidin-5-yl)-2-chloro-benzenesulfonamide;
trans-N-{4-[5-(2-Amino-4-methyl-pyrimidin-5-yl)-2-chloro-benzenesulfonylamino]-cyclohexyl}-acetamide;
cis-N-{4-[5-(2-Amino-4-methyl-pyrimidin-5-yl)-2-chloro-benzenesulfonylamino]-cyclohexyl}-acetamide;
5-(2-Amino-4-methyl-pyrimidin-5-yl)-2-chloro-N-(4-hydroxy-cyclohexyl)-benzenesulfonamide;
5-(2-Amino-4-methyl-pyrimidin-5-yl)-2-chloro-N-(5-trifluoromethyl-pyridin-2-yl)-benzenesulfonamide;
5-(2-Amino-4-methyl-pyridin-5-yl)-2-chloro-N-(6-methyl-pyridin-2-yl)-benzenesulfonamide;
5-(2-Amino-4-methyl-pyridin-5-yl)-2-chloro-N-(5-cano-pyridin-2-yl)-benzenesulfonamide;
5-(2-Amino-4-methyl-pyridin-5-yl)-2-chloro-N-(3-methyl-pyridin-2-yl)-benzenesulfonamide;
5-(2-Amino-4-methyl-pyridin-5-yl)-2-chloro-N-(5-fluoro-pyridin-2-yl)-benzenesulfonamide;
5-(2-Amino-4-methyl-pyridin-5-yl)-2-chloro-N-(5-chloro-pyridin-2-yl)-benzenesulfonamide;
5-(2-Amino-4-methyl-pyridin-5-yl)-2-chloro-N-(6-cyano-pyridin-3-yl)-benzenesulfonamide;
Pyridine-3-sulfonic acid [5-(2-amino-4-methyl-pyrimidin-5-yl)-2-chlorophenyl]-amide;
N-[5-(2-Amino-4-methyl-pyrimidin-5-yl)-2-chloro-phenyl]-3-chloro-benzene sulphonamide;
5-(2-Amino-4-methyl-pyrimidin-5-yl)-N-phenyl-2-trifluoromethyl-benzene sulphonamide;
5-(2-Amino-4-methyl-pyrimidin-5-yl)-N-benzo[1,3]dioxol-5-yl-2-trifluoromethyl-benzenesulfonamide;
5-(2-Amino-4-methyl-pyrimidin-5-yl)-N-(2,2-difluoro-benzo[1,3]dioxol-5-yl)-2-trifluoromethyl-benzenesulfonamide;
5-(2-Amino-4-methyl-pyrimidin-5-yl)-N-(trans-4-hydroxy-cyclohexyl)-2-trifluoromethyl-benzenesulfonamide;
5-(2-Amino-4-methyl-pyrimidin-5-yl)-N-(6-methyl-pyridin-2-yl)-2-trifluoromethyl-benzenesulfonamide;
5-(2-Amino-4-methyl-pyrimidin-5-yl)-N-(3,4-dimethyl-phenyl)-2-trifluoromethyl-benzenesulfonamide;
5-(2-Amino-4-methyl-pyrimidin-5-yl)-N-(3,4-dimethoxy-phenyl)-2-trifluoromethyl-benzenesulfonamide;
5-(2-Amino-4-methyl-pyrimidin-5-yl)-N-[trans-4-(methanesulfonylamino-methyl)-cyclohexyl]-2-trifluoromethyl-benzenesulfonamide;
5-(2-Amino-4-methyl-pyrimidin-5-yl)-N-{trans-4-[N,N-(dimethylamino)-sulfonylamino-methyl]-cyclohexyl}-2-trifluoromethyl-benzenesulfonamide;
5-(2-Amino-4-methyl-pyrimidin-5-yl)-N-(trans-4-hydroxymethyl-cyclohexyl)-2-trifluoromethyl-benzenesulfonamide;
trans-4-[5-(2-Amino-4-methyl-pyrimidin-5-yl)-2-trifluoromethyl-benzenesulfonylamino]-cyclohexanecarboxylic acid methyl ester;
5-(2-Amino-4-methyl-pyrimidin-5-yl)-N-(2-hydroxy-cyclohexyl)-2-trifluoromethyl-benzenesulfonamide;
5-(2-Amino-4-methyl-pyrimidin-5-yl)-N-(cis-4-hydroxy-cyclohexyl)-2-trifluoromethyl-benzenesulfonamide;
{trans-4-[5-(2-Amino-4-methyl-pyrimidin-5-yl)-2-trifluoromethyl-benzenesulfonylamino]-cyclohexyl}-carbamic acid tert-butyl ester;
5-(2-Amino-4-methyl-pyrimidin-5-yl)-N-((1S,2R)-2-hydroxy-cyclopentyl)-2-trifluoromethyl-benzenesulfonamide;
5-(2-Amino-4-methyl-pyrimidin-5-yl)-N-(4-tert-butyl-cyclohexyl)-2-trifluoromethyl-benzenesulfonamide;
5-(2-Amino-4-methyl-pyrimidin-5-yl)-N-((1S,2S)-2-hydroxy-cyclohexyl)-2-trifluoromethyl-benzenesulfonamide;
5-(2-Amino-4-methyl-pyrimidin-5-yl)-N-((1R,2S)-2-hydroxy-cyclopentyl)-2-trifluoromethyl-benzenesulfonamide;
5-(2-Amino-4-methyl-pyrimidin-5-yl)-2-trifluoromethyl-N-(1,3,5-trimethyl-1H-pyrazol-4-ylmethyl)-benzenesulfonamide;
5-(2-Amino-4-methyl-pyrimidin-5-yl)-N-(cis-4-hydroxymethyl-cyclohexyl)-2-trifluoromethyl-benzenesulfonamide;
5-(2-Amino-4-methyl-pyrimidin-5-yl)-N-((1R,2S)-2-hydroxy-cyclohexyl)-2-trifluoromethyl-benzenesulfonamide; and
5-(2-Amino-4-methyl-pyrimidin-5-yl)-2-chloro-N-(3-hydroxy-cyclohexyl)-benzene sulphonamide;
or a salt, suitably a pharmaceutically acceptable salt, or solvate thereof.

Many of the compounds represented by formula I are capable of forming acid addition salts, particularly pharmaceutically acceptable acid addition salts. Pharmaceutically acceptable acid addition salts of the compound of formula I include those of inorganic acids, for example, hydrohalic acids such as hydrofluoric acid, hydrochloric acid, hydrobromic acid or hydroiodic acid, nitric acid, sulfuric acid, phosphoric acid; and organic acids, for example aliphatic monocarboxylic acids such as formic acid, acetic acid, trifluoroacetic acid, propionic acid and butyric acid, aliphatic hydroxy acids such as lactic acid, citric acid, tartaric acid or malic acid, dicarboxylic acids such as maleic acid or succinic acid, aromatic carboxylic acids such as benzoic acid, p-chlorobenzoic acid, diphenylacetic acid or triphenylacetic acid, aromatic hydroxy acids such as o-hydroxybenzoic acid, p-hydroxybenzoic acid, 1-hydroxynaphthalene-2-carboxylic acid or 3-hydroxynaphthalene-2-carboxylic acid, and sulfonic acids such as methanesulfonic acid or benzenesulfonic acid. These salts may be prepared from compounds of formula I by known salt-forming procedures.

Compounds of formula I which contain acidic, e.g. carboxyl, groups, are also capable of forming salts with bases, in particular pharmaceutically acceptable bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine. These salts may be prepared from compounds of formula I by known salt-forming procedures.

Pharmaceutically acceptable solvates in accordance with the invention include those wherein the solvent of crystallisation may be isotopically substituted e.g. $D_2O$, $d_6$-acetone or $d_6$-DMSO.

Some compounds of the invention contain at least one asymmetric carbon atom and thus they exist in individual optically active isomeric forms or as mixtures thereof, e.g. as racemic mixtures. In cases where additional asymmetric centres exist the present invention also embraces both individual optically active isomers as well as mixtures, e.g. diastereomeric mixtures, thereof.

The invention includes all such forms, in particular the pure isomeric forms. The different isomeric forms may be separated or resolved one from the other by conventional methods, or any given isomer may be obtained by conventional synthetic methods or; by stereospecific or asymmetric syntheses. Since the compounds of the invention are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the invention.

The invention includes all pharmaceutically acceptable isotopically-labelled compounds of formula I wherein one or more atoms are replaced by atoms having the same atomic number, but an atomic mass or mass number different from the atomic mass or mass number usually found in nature. Examples of isotopes suitable for inclusion in the compounds of the invention include isotopes of hydrogen e.g. $^2H$ and $^3H$, carbon e.g. $^{11}C$, $^{13}C$ and $^{14}C$, chlorine e.g. $^{36}Cl$, fluorine e.g. $^{18}F$, iodine e.g. $^{123}I$ and $^{125}I$, nitrogen e.g. $^{13}N$ and $^{15}N$, oxygen e.g. $^{15}O$, $^{17}O$ and $^{18}O$, and sulfur e.g. $^{35}S$.

Certain isotopically-labelled compounds of formula I, for example those incorporating a radioactive isotope, are useful in drug and/or substrate tissue distribution studies. The radioactive isotopes tritium ($^3H$) and carbon-14 ($^{14}C$) are particularly useful for this purpose in view of their ease of incorporation and ready means of detection. Substitution with heavier isotopes such as deuterium ($^2H$) may afford certain therapeutic advantages that result from greater metabolic stability, for example increased in vivo half-life or reduced dosage requirements, and hence may be preferred in some circumstances. Substitution with positron emitting isotopes, such as $^{11}C$, $^{18}F$, $^{15}O$, and $^{13}N$ can be useful in Positron Emission Topography (PET) studies for examining substrate receptor occupancy.

Isotopically-labelled compounds of formula I can generally be prepared by conventional techniques known to those skilled in the art or by processes analogous to those described in the accompanying examples using an appropriate isotopically-labelled reagent in place of the non-labelled reagent previously used.

Some of the compounds of Formula I may exist in different tautomeric forms. Tautomerism is well known to those skilled in the art and the skilled person will readily appreciate which groups are able to tautomeric to form the different tautomeric forms. The invention includes all tautomeric forms of the compounds of Formula I.

Specific example compounds of formula I are described hereinafter in the Examples.

The invention provides, in another aspect, a process for preparing a compound of formula (I). For example, compounds of formula (I) where Ar' and $R^1$ are as defined above, A is $CR^3$ (where $R^3$ is as defined above) and B is N, are prepared in a 2-step synthesis from ketones using standard methods for preparing aminopyrimidines, according to Scheme 1.

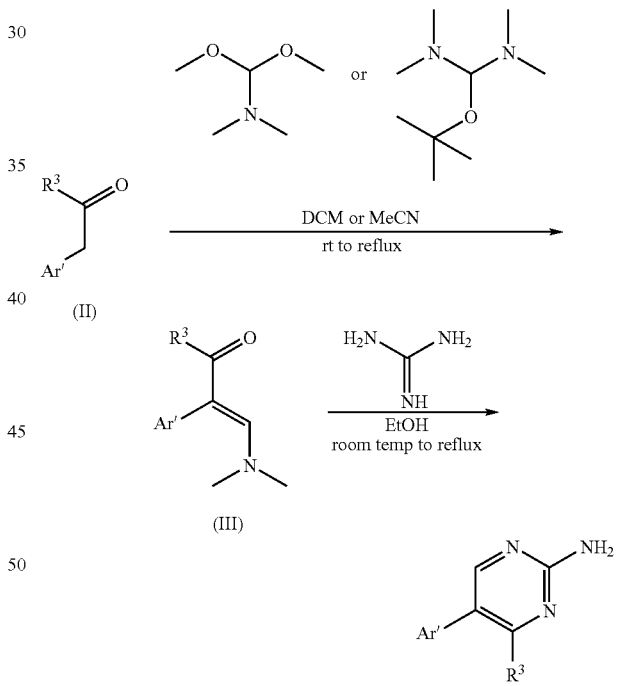

The ketones of formula (II) in the above reaction are commercially available, are described in the literature, e.g. WO03072557, WO03072557 or WO2004096797, or are readily prepared by methods well-known to those skilled in the art.

An alternative method of preparing compounds of formula (I), is shown in scheme 2. For example, compounds of formula (I) where A' and $R^1$ are as defined above, A is $CR^3$ and B is N, are prepared in a 2-step synthesis from aryl boronic acids or esters using standard methods for Suzuki coupling of heteroaryl halides with aryl boronates/boronic acids.

Scheme 2

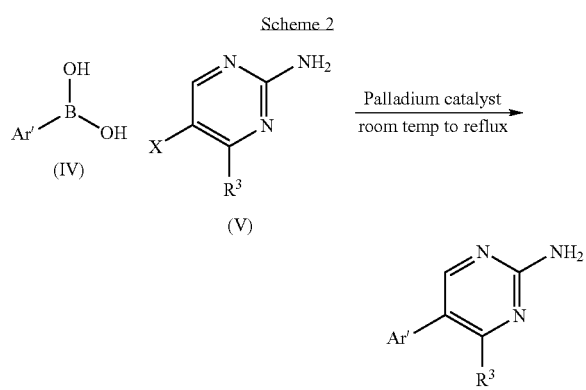

Yet another method of preparing compounds of formula (I), is shown in scheme 3. For example, compounds of formula (I) where Ar' and R¹ are as defined above, A is $CR^3$ and B is N, are prepared in a 2-step synthesis from aryl boronic acids or esters using standard methods for Suzuki coupling of heteroaryl halides with heteroaryl boronates/boronic acids.

Scheme 3

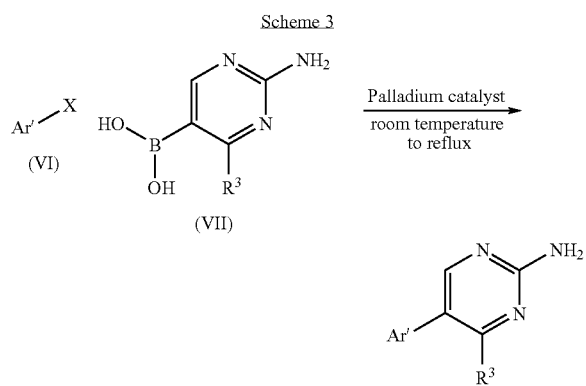

The aryl boronic acids of formula (IV), pyrimidyl halides of formula (V) (X=Br, I), aryl halides of formula (VI) (X=Cl, Br, I) and pyrimidines of formula (VII) in the above reactions are commercially available, are described in the literature, or are readily prepared by methods well-known to those skilled in the art.

Compounds of formula I and their pharmaceutically acceptable salts are useful as pharmaceuticals. In particular, they exhibit inhibition of phosphatidylinositol 3-kinase (PI 3-kinase) enzymes, especially the gamma isoform (p110γ), which are responsible for generating phosphorylated signalling products. Thus, the compounds of the present invention are useful in the treatment of disorders involving PI 3-kinase, particularly PI 3-kinase gamma isoform.

The inhibitory properties of compounds of formula I may be demonstrated in the following test procedures:

Baculovirus expressing different fragments of human PI 3-Kγ fused to glutathione S-transferase (GST) have been previously described by Stoyanova, S., Bulgarelli-Leva, G., Kirsch, C., Hanck, T., Klinger, R., Wetzker, R., Wymann, M. P. (1997) Lipid- and protein kinase activities of G protein-coupled PI 3-kinase g: structure-activity analysis and interactions with wortmannin. *Biochem. J.*, 324:489. Residues 38-1102 of human PI 3-Kγ are subcloned into the BamH1 and EcoR1 sites of the transfer vector pAcG2T (Pharmingen) to create a GST-PI 3-Kγ lacking the first 37 residues of PI 3-Kγ.

To express the recombinant protein, Sf9 (*Spodoptera frugiperda* 9) insect cells are routinely maintained at densities between $3\times10^5$ and $3\times10^6$ cells/ml in serum containing TNMFH medium (Sigma). Sf9 cells, at a density of $2\times10^6$ are infected with human GST-PI 3-KγΔ34 baculovirus at a multiplicity of infection (m.o.i.) of 1 for 72 hours. The infected cells are harvested by centrifugation at 1400 g for 4 minutes at 4° C. and the cell pellets are frozen at −80° C. Both Sf9 and Sf21 cells work equally well. Sf9 cells ($1\times10^9$) are resuspended in 100 ml cold (4° C.) lysis buffer (50 mM Tris-HCl pH 7.5, 1% Triton X-100, 150 mM NaCl, 1 mM NaF, 2 mM DTT and protease inhibitors. Cells are incubated on ice for 30 minutes then centrifuged at 15000 g for 20 minutes at 4° C. Purification of the supernatant sample is carried out at 4° C. by affinity chromatography using SEPHAROSE™ agarose gel beads coupled to glutathione (from Amersham Pharmacia Biotech). A cell lysate/GST resin ratio of 50:1 is used. The GST resin is firstly pre-rinsed to remove ethanol preservative and then equilibrated with lysis buffer. Cell lysate (supernatant) is added (usually as 50 ml lysate to 1 ml GST resin in 50 ml tubes) and gently rotated on a mixer at 4° C. for 2-3 hours. The unbound flow through sample is collected by centrifugation at 1000 g for 5 minutes at 4° C. using a DENLEY™ centrifuge. The 1 ml GST resin containing bound material is transferred to a 15 ml FALCON™ centrifuge tube for subsequent washing and elution steps. Firstly a series of 3 cycles of washings (mixing by gentle inversion) is performed with 15 ml ice cold wash Buffer A (50 mM Tris-HCl pH 7.5, 1% Triton X-100, 2 mM DTT) interspersed with centrifugation at 1000 g for 5 minutes at 4° C. A final single wash step is performed with 15 ml ice cold wash Buffer B (50 mM Tris-HCl pH 7.5, 2 mM DTT) and then centrifuged at 1050 g for 5 minutes at 4° C. The washed GST resin is finally eluted with 4 cycles of 1 ml ice cold elution buffer (50 mM Tris-HCl pH 7.5, 10 mM reduced glutathione, 2 mM DTT, 150 mM NaCl, 1 mM NaF, 50% ethylene glycol and protease inhibitors) interspersed with centrifugation at 1000 g for 5 minutes at 4° C. Samples are aliquoted and stored at −20° C.

An in vitro kinase assay was established that measures the transfer of the terminal phosphate of adenosine triphosphate to phosphatidylinositol. The kinase reaction is performed in a white 96 well microtitre plate as a Scintillation Proximity Assay. Each well contains 10 μl test compound in 5% dimethylsulphoxide and 20 μl assay mix (40 mM Tris, 200 mM NaCl, 2 mM ethyleneglycol-aminoethyl-tetraacetic acid (EGTA), 15 μg/ml phosphatidylinositol, 12.5 μM adenosine triphosphate (ATP), 25 mM $MgCl_2$, 0.1 μCi [$^{33}$P]ATP). The reaction is started by the addition of 20 μl of enzyme mix (40 mM Tris, 200 mM NaCl, 2 mM EGTA containing recombinant GST-p110γ). The plate is incubated at room temperature for 60 minutes and the reaction terminated by the adding 150 μl of WGA-bead stop solution (40 mM Tris, 200 mM NaCl, 2 mM EGTA, 1.3 mM ethylene diamine tetraacetic acid (EDTA), 2.6 μM ATP and 0.5 mg of Wheat Germ Agglutinin-SPA beads (Amersham Biosciences) to each well. The plate is sealed, incubated at room temperature for 60 minutes, centrifuged at 1200 rpm and then counted for 1 minute using a scintillation counter. Total activity is determined by adding 10 μl of 5% dimethylsulphoxide (DMSO) and non-specific activity is determined by adding 10 μl 50 mM EDTA in place of the test compound.

All of the Example compounds have an $IC_{50}$ of less than 10 μM in the aforementioned assay. Substantially all compounds of the Examples herein below have $IC_{50}$ values from about 0.004 to 1.113 μM in the aforementioned assay. The following specific Example compounds have $IC_{50}$ values as follows: Examples 1-1, 1-15, 1-30, 1-50, 2-1, 3-1, 3-17, 3-35 and 3-53 have IC$_{50}$ values of 0.004, 0.239, 0.135, 0.050, 0.223, 0.219, 0.305, 0.016 and 0.108 μM respectively.

Having regard to their inhibition of phosphatidylinositol 3-kinase enzymes, compounds of formula I in free or pharmaceutically acceptable salt form, hereinafter alternately referred to as "agents of the invention", are useful in the treatment of conditions which are mediated by the activation of the PI 3-kinase enzymes, particularly inflammatory or allergic conditions. Treatment in accordance with the invention may be symptomatic or prophylactic.

Accordingly, agents of the invention are useful in the treatment of inflammatory or obstructive airways diseases, resulting, for example, in reduction of tissue damage, airways inflammation, bronchial hyperreactivity, remodelling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant form any previously administered symptomatic asthma therapy.

Other inflammatory or obstructive airways diseases and conditions to which the present invention is applicable include acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Having regard to their anti-inflammatory activity, in particular in relation to inhibition of eosinophil activation, agents of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Löffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosiniophil-related disorders affecting the airways occasioned by drug-reaction.

Agents of the invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemnphisus, epidermolysis bullosa acquisita, and other inflammatory or allergic conditions of the skin.

Agents of the invention may also be used for the treatment of other diseases or conditions, in particular diseases or conditions having an inflammatory component, for example, treatment of diseases and conditions of the eye such as conjunctivitis, keratoconjunctivitis sicca, and vernal conjunctivitis, diseases affecting the nose including allergic rhinitis, and inflammatory disease in which autoimmune reactions are implicated or having an autoimmune component or aetiology, including autoimmune haematological disorders (e.g. haemnolytic anaemia, aplastic anaemia, pure red cell anaemia and idiopathic thrombocytopenia), systemic lupus erythematosus, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine ophthalmopathy, Grave's disease, sarcoidosis, alveolitis, chronic hypersensitivity pneumonitis, multiple sclerosis, primary billiary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy).

Other diseases or conditions which may be treated with agents of the invention include thrombosis, hypertension, heart ischaemia and pancreatitis, (Nature review November 2006 Vol 5), treatment of anaemia including haemolytic anaemia, aplastic anaemia and pure red cell anaemia (WO 2006/040318), septic shock, rheumatoid arthritis, osteoarthritis, proliferative diseases such as cancer, atherosclerosis, allograft rejection following transplantation, stroke, obesity, restenosis, diabetes, e.g. diabetes mellitus type I (juvenile diabetes) and diabetes mellitus type II, diarrheal diseases, ischemia/reperfusion injuries, retinopathy, such as diabetic retinopathy or hyperbaric oxygen-induced retinopathy, and conditions characterised by elevated intraocular pressure or secretion of ocular aqueous humor, such as glaucoma.

Agents of the present invention may be useful in the treatment or prevention of heart failure such as (acute and chronic) congestive heart failure, left ventricular dysfunction including impaired cardiac contractility, hypertrophic cardiomyopathy, diabetic cardiac myopathy and other types of detrimental cardiac dysfunction and remodeling.

Other diseases or conditions which may be treated with agents of the invention include septic shock, rheumatoid arthritis, osteoarthritis, proliferative diseases such as cancer, atherosclerosis, allograft rejection following transplantation, stroke, obesity, restenosis, diabetes, e.g. diabetes mellitus type I (juvenile diabetes) and diabetes mellitus type II, diarrheal diseases, ischemia/reperfusion injuries, retinopathy, such as diabetic retinopathy or hyperbaric oxygen-induced retinopathy, and conditions characterised by elevated intraocular pressure or secretion of ocular aqueous humor, such as glaucoma.

The agents of the invention may also be useful in the treatment of visceral disorders, inflammatory bowel disease, inflammatory bowel disorder, cystitis, e.g. interstitial cystitis and urinary incontinence including bladder detrusor hyperreflexia and bladder hypersensitivity.

The effectiveness of an agent of the invention in inhibiting inflammatory conditions, for example in inflammatory airways diseases, may be demonstrated in an animal model, e.g. a mouse or rat model, of airways inflammation or other inflammatory conditions, for example as described by Szarka et al, *J. Immunol. Methods* (1997) 202:49-57; Renzi et al, *Am. Rev. Respir. Dis.* (1993) 148:932-939; Tsnyuki et al., *J. Clin. Invest.* (1995) 96:2924-2931; and Cernadas et al (1999) *Am. J. Respir. Cell Mol. Biol.* 20:1-8.

The agents of the invention are also useful as co-therapeutic agents for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. An agent of the invention may be mixed with the other drug substance in a fixed pharmaceutical composition or it may be administered separately, before, simultaneously with or after the other drug substance. Accordingly the invention includes a combination of an agent of the invention as hereinbefore described with an anti-inflammatory, bronchodilatory or antihistamine drug substance, said agent of the invention and said drug substance being in the same or different pharmaceutical composition. Such anti-inflammatory drugs include steroids, in particular glucocorticosteroids such as budesonide, beclamethasone dipropionate, fluticasone propionate, ciclesonide or mometasone furoate and compounds described in WO 0200679, WO 0288167, WO 0212266 and WO 02100879, LTB4 antagonists such as those described in U.S. Pat. No. 5,451,700, LTD4 antagonists such as montelukast and zafirlukast, dopamine receptor agonists such as cabergoline, bromocriptine, ropinirole and 4-hydroxy-7-[2-[[2-[[3-(2-phenylethoxy)-propyl]-sulfonyl]ethyl]-amino]ethyl]-2(3H)-benzothiazolone and pharmaceutically acceptable salts thereof (the hydrochloride being Viozan®—AstraZeneca), and PDE4 inhibitors such as Ariflo® (GlaxoSmithKline), Roflumilast (Byk Gulden), V-11294A (Napp), BAY19-8004 (Bayer), SCH-351591 (Schering-Plough), Arofylline (Almirall Prodesfarma), PD189659 (Parke-Davis), AWD-12-281 (Asta Medica), CDC-801 (Celgene) and KW-4490 (Kyowa Hakko Kogyo) as well as those described in WO 98/18796 and WO 03/39544. Such bronchodilatory drugs include anticholinergic or antimuscarinic agents, in particular ipratropium bromide, oxitropium bromide and tiotropium salts but also those described in WO 01/04118, WO 02/51841, WO 02/53564, WO 03/00840, WO 03/87094, WO 04/05285, WO 02/00652, WO 03/53966, EP 424021, U.S. Pat. No. 5,171, 744, U.S. Pat. No. 3,714,357 and WO 03/33495, and beta-2 adrenoceptor agonists such as salbutamol, terbutaline, salmeterol and, especially, formoterol and pharmaceutically acceptable salts thereof, and compounds (in free or salt or solvate form) of formula I of PCT International patent publication No. WO 00/75114, which document is incorporated herein by reference, preferably compounds of the Examples thereof, especially 5-[(R)-2-(5,6-Diethyl-indan-2-ylamino)-1-hydroxy-ethyl]-8-hydroxy-1H-quinolin-2-one, and pharmaceutically acceptable salts thereof. Co-therapeutic antihistamine drug substances include cetirizine hydrochloride, acetaminophen, clemastine fumarate, promethazine, loratidine, desloratidine, diphenhydramine and fexofenadine hydrochloride. Combinations of agents of the invention and steroids, beta-2 agonists, PDE4 inhibitors or LTD4 antagonists may be used, for example, in the treatment of COPD or, particularly, asthma. Combinations of agents of the invention and anticholinergic or antimuscarinic agents, PDE4 inhibitors, dopamine receptor agonists or LTB4 antagonists may be used, for example, in the treatment of asthma or, particularly, COPD.

Other useful combinations of agents of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CCR3, CXCR4, CXCR5, particularly CCR-5 antagonists such as Schering-Plough antagonists SC-351125, SCH-55700 and SCH-D, Takeda antagonists such as N-[[4-[[[6,7-dihydro-2-(4-methylphenyl)-5H-benzocyclohepten-8-yl]carbonyl]amino]phenyl]-methyl]tetrahydro-N,N-dimethyl-2H-pyran-4-aminium chloride (TAK-770), and CCR-5 antagonists described in U.S. Pat. No. 6,166,037 (particularly claims 18 and 19), WO00/66558 (particularly claim 8), and WO00/66559 (particularly claim 9).

Pi3 kinase inhibitors, e.g. those compounds of the invention, may be combined with an angiotensin receptor blocker, e.g. valsartan (an angiotensin receptor blocker) and achieve greater therapeutic effect than the administration of valsartan alone. The combination regimen also surprisingly reduces the rate of progression of cardiac, renal and cerebral end-organ damage. The combination elicits enhanced antihypertensive effects (whether malignant, essential, reno-vascular, diabetic, isolated systolic, or other secondary type of hypertension) and lessening of pulse pressure. The combination is also effective in treating supraventricular and ventricular arrhythmias, atrial fibrillation, atrial flutter or detrimental vascular remodeling. It can further be shown that the combination is beneficial in the treatment and prevention of myocardial infarction and its sequelae, and is useful in treating atherosclerosis, angina (whether stable or unstable), renal insufficiency (diabetic and non-diabetic), peripheral vascular disease, cognitive dysfunction, and stroke. Furthermore, the improvement in endothelial function with the combination therapy provides benefit in diseases in which normal endothelial function is disrupted such as heart failure, angina pectoris and diabetes. Furthermore, the combination may be used for the treatment or prevention of primary and secondary pulmonary hypertension, renal failure conditions, such as diabetic nephropathy, glomerulonephritis, scleroderma, glomerular sclerosis, proteinuria of primary renal disease, and also renal vascular hypertension, diabetic retinopathy, the management of other vascular disorders, such as migraine, peripheral vascular disease, Raynaud's disease, luminal hyperplasia, cognitive dysfunction (such as Alzheimer's), glaucoma and stroke.

Agents of the invention may also be useful in the treatment of diseases or disorders mediated by lymphocytes interactions, e.g. in transplantation, such as acute or chronic rejection of cell, tissue or organ allo- or xenografts or delayed graft function, graft versus host disease, autoimmune diseases, e.g. rheumatoid arthritis, systemic lupus erythematosus, hashimoto's thyroidis, multiple sclerosis, myasthenia gravis, diabetes type I or II and the disorders associated therewith, vasculitis, pernicious anemia, Sjoegren syndrome, uveitis, Graves ophthalmopathy, alopecia areata and others, inflammatory diseases optionally with underlying aberrant reactions, e.g. inflammatory bowel disease, Crohn's disease or ulcerative colitis, intrinsic asthma, inflammatory lung injury, inflammatory liver injury, inflammatory glomerular injury, atherosclerosis, osteoarthritis and further eczematous dermatitises, seborrhoeic dermatitis, cutaneous manifestations of immunologically-mediated disorders, inflammatory eye disease, myocarditis or hepatitis, gut ischemia, traumatic shock, cancer, e.g. breast cancer, T cell lymphomas or T cell leukemias, infectious diseases, e.g. toxic shock (e.g. superantigen induced), septic shock, adult respiratory distress syndrome or viral infections, e.g. AIDS, viral hepatitis, chronic bacterial infection, or senile dementia. Examples of cell, tissue or solid organ transplants include e.g. pancreatic islets, stem cells, bone marrow, corneal tissue, neuronal tissue, heart, lung, combined heart-lung, kidney, liver, bowel, pancreas, trachea or oesophagus.

Agents of the invention may be administered in conjunction with, e.g. as an adjuvant to, other drugs e.g. immunosuppressive or immunomodulating agents or other anti-inflammatory agents, e.g. for the treatment or prevention of allo- or xenograft acute or chronic rejection or inflammatory or autoimmune disorders. For example, the compounds of formula I may be used in combination with a calcineurin inhibitor, e.g. cyclosporin A or FK 506; a mTOR inhibitor, e.g. rapamycin, 40-O-(2-hydroxyethyl)-rapamycin, CCI779, ABT578, AP23573, biolimus-7 or biolimus-9; an ascomycin having immuno-suppressive properties, e.g. ABT-281 or ASM981; corticosteroids; cyclophosphamide; azathioprene; methotrexate; leflunomide; mizoribine; mycophenolic acid or salt; mycophenolate mofetil; 15-deoxyspergualin or an immunosuppressive homologue, analogue or derivative thereof; a PKC inhibitor, e.g. as disclosed in WO 02/38561 or WO 03/82859, e.g. the compound of Example 56 or 70; a JAK3 kinase inhibitor, e.g. N-benzyl-3,4-dihydroxy-benzylidene-cyanoacetamide α-cyano-(3,4-dihydroxy)-]N-benzylcinnamamide (Tyrphostin AG 490), prodigiosin 25-C (PNU156804), [4-(4'-hydroxyphenyl)-amino-6,7-dimethoxyquinazoline] (WHI-P131), [4-(3'-bromo-4'-hydroxyphenyl)-amino-6,7-dimethoxyquinazoline] (WHI-P154), [4-(3', 5'-dibromo-4'-hydroxyphenyl)-amino-6,7-dimethoxyquinazoline] WHI-P97, KRX-211, 3-{(3R,4R)-4-methyl-3-[methyl-(7H-pyrrolo[2,3-d]pyrimidin-4-yl)-amino]-piperidin-1-yl}-3-oxo-propionitrile, in free form or in a pharmaceutically acceptable salt form, e.g. mono-citrate (also called CP-690,550), or a compound as disclosed in WO 04/052359 or WO 05/066156; a S1P receptor agonist or modulator, e.g. FTY720 optionally phosphorylated or an analog thereof, e.g. 2-amino-2-[4-(3-benzyloxyphenylthio)-2-chlorophenyl]ethyl-1,3-propanediol optionally phosphorylated or 1-{4-[1-(4-cyclohexyl-3-trifluoromethyl-benzyloxyimino)-ethyl]-2-ethyl-benzyl}-azetidine-3-carboxylic acid or its pharmaceutically acceptable salts; immunosuppressive monoclonal antibodies, e.g., monoclonal antibodies to leukocyte receptors, e.g., MHC, CD2, CD3, CD4, CD7, CD8, CD25, CD28, CD40, CD45, CD52, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists.

The agents of the invention may also be useful in the treatment of visceral disorders, inflammatory bowel disease, inflammatory bowel disorder, cystitis, e.g. interstitial cystitis and urinary incontinence including bladder detrusor hyperreflexia and bladder hypersensitivity.

The agents of the invention may also be used in the treatment of anemia, according to WO2006/040318.

The agents of the invention may be administered by any appropriate route, e.g. orally, for example in the form of a tablet or capsule; parenterally, for example intravenously; by inhalation, for example in the treatment of inflammatory or obstructive airways disease; intranasally, for example in the treatment of allergic rhinitis; topically to the skin, for example in the treatment of atopic dermatitis; or rectally, for example in the treatment of inflammatory bowel disease.

The present invention also provides a pharmaceutical composition comprising a compound of formula I in free form or in the form of a pharmaceutically acceptable salt, optionally together with a pharmaceutically acceptable diluent or carrier therefor. The composition may contain a co-therapeutic agent, such as an anti-inflammatory, bronchodilatory or antihistamine drug as hereinbefore described. Such compositions may be prepared using conventional diluents or excipients and techniques known in the galenic art. Thus oral dosage forms may include tablets and capsules.

Formulations for topical administration may take the form of creams, ointments, gels or transdermal delivery systems, e.g. patches. Compositions for inhalation may comprise aerosol or other atomizable formulations or dry powder formulations.

When the composition comprises an aerosol formulation, it preferably contains, for example, a hydro-fluoro-alkane (HFA) propellant such as HFA134a or HFA227 or a mixture of these, and may contain one or more co-solvents known in the art such as ethanol (up to 20% by weight), and/or one or more surfactants such as oleic acid or sorbitan trioleate, and/or one or more bulking agents such as lactose. When the composition comprises a dry powder formulation, it preferably contains, for example, the compound of formula I having a particle diameter up to 10 microns, optionally together with a diluent or carrier, such as lactose, of the desired particle size distribution and a compound that helps to protect against product performance deterioration due to moisture. When the composition comprises a nebulised formulation, it preferably contains, for example, the compound of formula I either dissolved, or suspended, in a vehicle containing water, a co-solvent such as ethanol or propylene glycol and a stabiliser, which may be a surfactant.

Dosages of agents of the invention employed in practising the present invention will of course vary depending, for example, on the particular condition to be treated, the effect desired and the node of administration. In general, suitable daily dosages for oral administration are of the order of 0.1 to 10 mg/kg.

EXAMPLES
Preparation of Final Compounds
Compounds of formula (VIII) which are compounds of formula (I)
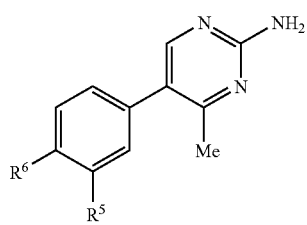
are shown in Table 1 below, the method of preparation being described hereinafter. The table also shows mass spectrometry data.
TABLE 1
| Ex. | $R^6$ | $R^5$ | M/s [M + H]$^+$ |
|---|---|---|---|
| 1-1 | Cl | 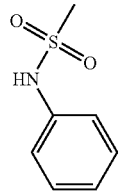 | 375.19 |
| 1-2 | Br | 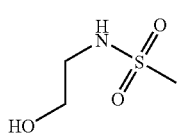 | 387.15 |
| 1-3 | Br | 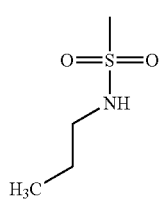 | 387.19 |
| 1-4 | Br | 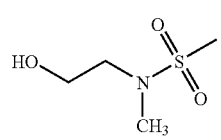 | 403.19 |
| 1-5 | Cl | 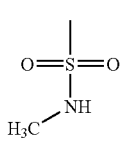 | 313.37 |
| 1-6 | CH$_3$ | | 355.23 |
| 1-7 | F | | 359.25 |
| 1-8 | Br | | 417.2 |
| 1-9 | Cl | | 357.18 |
| 1-10 | Br | | 403.17 |
| 1-11 | Cl | | 357.23 |
| 1-12 | Cl | | 353.25 |

TABLE 1-continued
| Ex. | R6 | R5 | M/s [M + H]+ |
|---|---|---|---|
| 1-13 | O—CH3 | 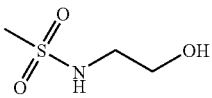 | 339.25 |
| 1-14 | Br | 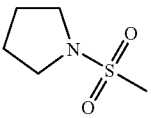 | 399.17 |
| 1-15 | Cl | 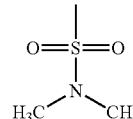 | 327.22 |
| 1-16 | Cl | 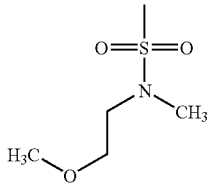 | 371.25 |
| 1-17 | CH3 | 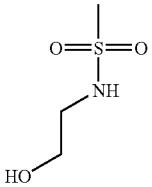 | 323.17 |
| 1-18 | Br | 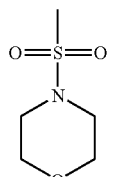 | 415.19 |
| 1-19 | Br | 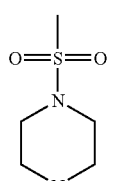 | 428.22 |
| 1-20 | Br | 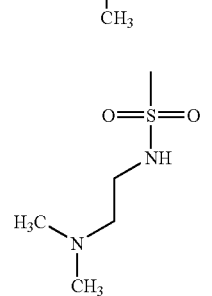 | 416.19 |
| 1-21 | CH3 | 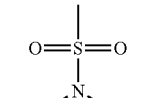 | 307.17 |
| 1-22 | CH3 | 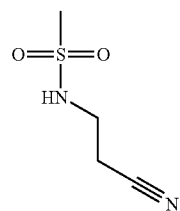 | 332.21 |
| 1-23 | Cl | 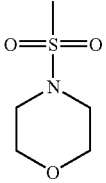 | 369.19 |
| 1-24 | F | 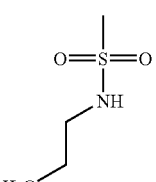 | 325.24 |
| 1-25 | F | 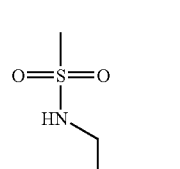 | 336.21 |
| 1-26 | CH3 | 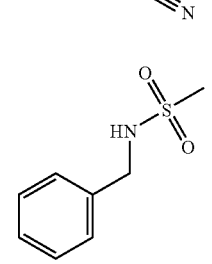 | 369.24 |
| 1-27 | Cl | 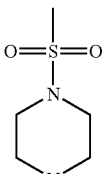 | 382.22 |

TABLE 1-continued

| Ex. | R⁶ | R⁵ | M/s [M + H]⁺ |
|---|---|---|---|
| 1-28 | F | N-methyl-N-(2-methoxyethyl)methanesulfonamide | 355.25 |
| 1-29 | Cl | N-(2-hydroxyethyl)methanesulfonamide | 343.05 |
| 1-30 | Cl | 1-(methanesulfonyl)azetidin-3-ol | 355.01 |
| 1-31 | Br | N,N-dimethylmethanesulfonamide | 373.19 |
| 1-32 | Cl | 1-(methanesulfonyl)-4-ethylpiperazine | 396.68 |
| 1-33 | Cl | 1-(methanesulfonyl)-4-isopropylpiperazine | 410.72 |
| 1-34 | Cl | N-cyclohexylmethanesulfonamide | 381.09 |
| 1-35 | Cl | N-(2-cyanoethyl)methanesulfonamide | 352.02 |
| 1-36 | Cl | N-cyclopentylmethanesulfonamide | 367.04 |
| 1-37 | Cl | N-(2-morpholinoethyl)methanesulfonamide | 412.13 |
| 1-38 | Cl | N-benzylmethanesulfonamide | 389.07 |
| 1-39 | Cl | N-(3-cyanophenyl)methanesulfonamide | 400.12 |
| 1-40 | Cl | N-methyl-N-(3-(trifluoromethyl)phenyl)methanesulfonamide | 457.14 |

TABLE 1-continued

| Ex. | R⁶ | R⁵ | M/s [M + H]⁺ |
|---|---|---|---|
| 1-41 | Cl | N-(4-fluoro-3-methylphenyl)methanesulfonamide | 407.14 |
| 1-42 | Cl | N-(3-(trifluoromethyl)phenyl)methanesulfonamide | 443.13 |
| 1-43 | Cl | N-(4-chlorophenyl)methanesulfonamide | 409.09 |
| 1-44 | Cl | N-(4-chlorophenyl)-N-methylmethanesulfonamide | 423.07 |
| 1-45 | Cl | N-(3,4-dichlorophenyl)-N-methylmethanesulfonamide | 459.03 |
| 1-46 | Cl | N-methyl-N-phenylmethanesulfonamide | 389.05 |
| 1-47 | Cl | N-(benzo[d][1,3]dioxol-5-yl)-N-methylmethanesulfonamide | 433.04 |
| 1-48 | Cl | N-(3-(1H-imidazol-1-yl)phenyl)methanesulfonamide | 440.22 |
| 1-49 | Cl | N-methylmethanesulfonamide | 313.16 |
| 1-50 | Cl | N-methylbenzenesulfonamide | 375.06 |
| 1-51 | Cl | N-(tetrahydro-2H-pyran-4-yl)methanesulfonamide | 383.12 |
| 1-52 | Cl | N-cycloheptylmethanesulfonamide | 394.92 |
| 1-53 | Cl | 1-(methylsulfonyl)piperidin-4-ol | 383.11 |
| 1-54 | Cl | N-(benzo[d][1,3]dioxol-5-yl)methanesulfonamide | 419.07 |

TABLE 1-continued

| Ex. | R⁶ | R⁵ | M/s [M + H]⁺ |
|---|---|---|---|
| 1-55 | Cl | (N-pyridin-3-yl methanesulfonamide) | 419.07 |

Further preferred compounds of the present invention are as shown in Table 2 below. The methods of preparation being described thereinafter.

TABLE 2

| Ex. | Chemical Structure | Chemical Name | M/s [M + H]⁺ |
|---|---|---|---|
| 2-1 | 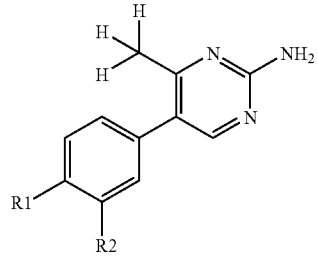 | 2-tert-Butyl-4'-methyl-[4,5']bipyrimidinyl-2'-ylamine | 244.27 |

Yet further preferred compounds of formula (I) which are of formula (IX)

$$\text{(IX)}$$

(structure: 2-amino-4-methyl-5-(3,4-disubstituted-phenyl)pyrimidine with R1, R2 substituents)

are as shown in Table 3 below:

| Ex. | R¹ | R² | M/s [M + H]⁺ |
|---|---|---|---|
| 3-1 | Cl | N-cyclopropyl methanesulfonamide | 338.81 |
| 3-2 | Cl | N-cyclobutyl methanesulfonamide | 352.80 |
| 3-3 | Cl | azetidin-1-yl methanesulfonyl | 338.79 |
| 3-4 | Cl | N-(bicyclo[2.2.2]octyl) methanesulfonamide | 406.94 |
| 3-5 | Cl | N-(2-hydroxycyclohexyl) methanesulfonamide | 396.91 |
| 3-6 | Cl | N-(4,4-difluorocyclohexyl) methanesulfonamide | 417.06 |
| 3-7 | Cl | N-(3-hydroxyadamantan-1-ylmethyl) methanesulfonamide | 449.6 |
| 3-8 | Cl | N-(3-hydroxyadamantan-1-yl) methanesulfonamide | 449.1 |
| 3-9 | Cl | N-neopentyl methanesulfonamide | 368.85 |

-continued
| Ex. | R¹ | R² | M/s [M + H]⁺ |
|---|---|---|---|
| 3-10 | Cl | 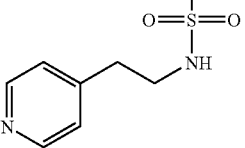 | 404.36 |
| 3-11 | Cl | 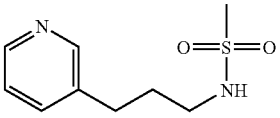 | 418.35 |
| 3-12 | Cl | 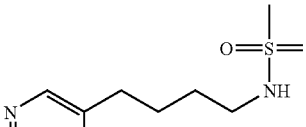 | 432.26 |
| 3-13 | Cl | 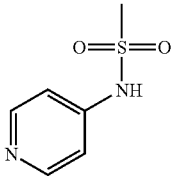 | 375.97 |
| 3-14 | Cl | 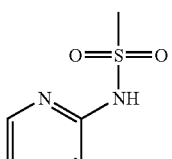 | 376.06 |
| 3-15 | Cl | 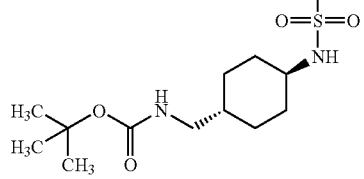 | 509.7 |
| 3-16 | Cl | 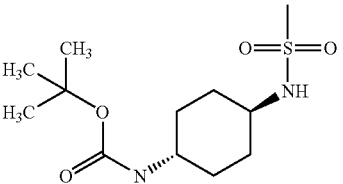 | 496.4 |
| 3-17 | Cl | 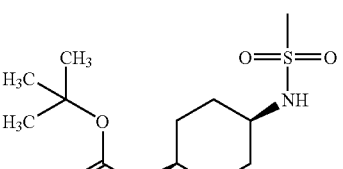 | 496.38 |
-continued
| Ex. | R¹ | R² | M/s [M + H]⁺ |
|---|---|---|---|
| 3-18 | Cl | 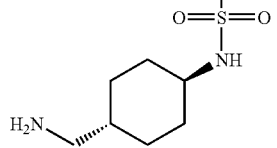 | 409.8 |
| 3-19 | Cl | 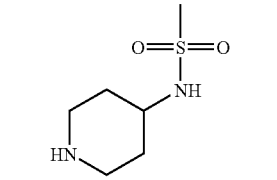 | 382.08 |
| 3-20 | Cl | 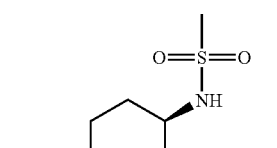 | 395.87 |
| 3-21 | Cl | 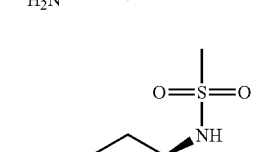 | 395.87 |
| 3-22 | Cl | 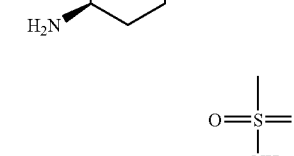 | 452.38 |
| 3-23 | Cl | 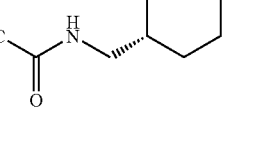 | 424.1 |
| 3-24 | Cl | 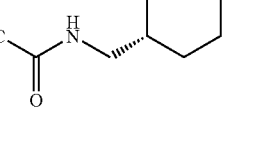 | 437.94– |

-continued

| Ex. | R¹ | R² | M/s [M + H]⁺ |
|---|---|---|---|
| 3-25 | Cl | cyclohexane-1,4-diyl with NHS(O)₂CH₃ and NHC(O)CH₃ | 437.94 |
| 3-26 | Cl | 4-hydroxycyclohexyl-NH-S(O)₂CH₃ | 397.41 |
| 3-27 | Cl | 5-(trifluoromethyl)pyridin-2-yl-NH-S(O)₂CH₃ | 442.07 |
| 3-28 | Cl | 6-methylpyridin-2-yl-NH-S(O)₂CH₃ | 388.04 |
| 3-29 | Cl | 5-cyanopyridin-2-yl-NH-S(O)₂CH₃ | 399.10 |
| 3-30 | Cl | 3-methylpyridin-2-yl-NH-S(O)₂CH₃ | 388.10 |
| 3-31 | Cl | 5-chloropyridin-2-yl-NH-S(O)₂CH₃ | 407.94 |
| 3-32 | Cl | 5-fluoropyridin-2-yl-NH-S(O)₂CH₃ | 391.99 |
| 3-33 | Cl | 6-cyanopyridin-3-yl-NH-S(O)₂CH₃ | 399.00 |
| 3-34 | Cl | pyridin-3-yl-S(O)₂-NHCH₃ | 374.02 |
| 3-35 | Cl | 3-chlorophenyl-S(O)₂-NHCH₃ | 407.00 |
| 3-36 | CF₃ | phenyl-NH-S(O)₂CH₃ | 409.00 |
| 3-37 | CF₃ | benzo[1,3]dioxol-5-yl-NH-S(O)₂CH₃ | 452.97 |
| 3-38 | CF₃ | 2,2-difluorobenzo[1,3]dioxol-5-yl-NH-S(O)₂CH₃ | 488.98 |
| 3-39 | CF₃ | trans-4-hydroxycyclohexyl-NH-S(O)₂CH₃ | 431.11 |

-continued

| Ex. | R¹ | R² | M/s [M + H]⁺ |
|---|---|---|---|
| 3-40 | CF₃ | 3-methylphenyl-NH-SO₂-CH₃ | 424.09 |
| 3-41 | CF₃ | 3,4-dimethylphenyl-NH-SO₂-CH₃ | 437.04 |
| 3-42 | CF₃ | 3,4-dimethoxyphenyl-NH-SO₂-CH₃ | 469.03 |
| 3-43 | CF₃ | trans-4-(methanesulfonylaminomethyl)cyclohexyl-NH-SO₂-CH₃ | 522.05 |
| 3-44 | CF₃ | trans-4-((dimethylsulfamoyl)aminomethyl)cyclohexyl-NH-SO₂-CH₃ | 551.05 |
| 3-45 | CF₃ | trans-4-(hydroxymethyl)cyclohexyl-NH-SO₂-CH₃ | 445.07 |
| 3-46 | CF₃ | trans-4-(methoxycarbonyl)cyclohexyl-NH-SO₂-CH₃ | 473.05 |

-continued

| Ex. | R¹ | R² | M/s [M + H]⁺ |
|---|---|---|---|
| 3-47 | CF₃ | 2-hydroxycyclohexyl-NH-SO₂-CH₃ | 431.05 |
| 3-48 | CF₃ | trans-4-hydroxycyclohexyl-NH-SO₂-CH₃ | 431.11 |
| 3-49 | CF₃ | trans-4-(tert-butoxycarbonylamino)cyclohexyl-NH-SO₂-CH₃ | 530.06 |
| 3-50 | CF₃ | 2-hydroxycyclopentyl-NH-SO₂-CH₃ | 417.09 |
| 3-51 | CF₃ | 4-tert-butylcyclohexyl-NH-SO₂-CH₃ | 471.09 |
| 3-52 | CF₃ | 2-hydroxycyclohexyl-NH-SO₂-CH₃ | 431.11 |
| 3-53 | CF₃ | 2-hydroxycyclopentyl-NH-SO₂-CH₃ | 417.03 |

-continued

| Ex. | R¹ | R² | M/s [M + H]⁺ |
|---|---|---|---|
| 3-54 | CF₃ | sulfonamide-CH₂-(1,3,5-trimethyl-pyrazol-4-yl) | 455.07 |
| 3-55 | CF₃ | sulfonamide-(4-hydroxymethyl-cyclohexyl) | 445.06 |
| 3-56 | CF₃ | sulfonamide-(2-hydroxy-cyclohexyl) | 431.10 |
| 3-57 | Cl | sulfonamide-(3-hydroxy-cyclohexyl) | 397.5 |

Referring to the examples that follow, compounds of the preferred embodiments are synthesized using the methods described herein, or other methods, which are known in the art.

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

It is understood that the invention is not limited to the embodiments set forth herein for illustration, but embraces all such forms thereof as come within the scope of the above disclosure.

General Conditions:

Mass spectra are run on LCMS systems using electrospray ionization. These are either Agilent 1100 HPLC/Micromass Platform Mass Spectrometer combinations or Waters Acquity HPLC with SQD Mass Spectrometer. [M+H]⁺ refers to mono-isotopic molecular weights.

NMR spectra are run on open access Bruker AVANCE 400 NMR spectrometers using ICON-NMR. Spectra are measured at 298K and are referenced using the solvent peak.

The various starting materials, intermediates, and compounds of the preferred embodiments may be isolated and purified, where appropriate, using conventional techniques such as precipitation, filtration, crystallization, evaporation, distillation, and chromatography. Unless otherwise stated, all starting materials are obtained from commercial suppliers and used without further purification. Salts may be prepared from compounds by known salt-forming procedures.

In addition various trade reagents and materials available from have been utilized. Such reagents and materials can be readily obtained from the suppliers indicated.

For the examples below as well as throughout the application, the following abbreviations have the following meanings. If not defined, the terms have their generally accepted meanings.

Abbreviations:
DMF dimethyl-formamide
DIPEA diisopropylethylamine
h hour
min minutes
NMP N-methylpyrrolidine
THF tetrahydrofuran
MeOH methanol
DCM dichloromethane
EtOAc ethyl acetate
EtOH ethanol
LCMS liquid chromatographic mass spectroscopy
TEA triethylamine
TFA trifluoroacetic acid
HPLC high performance liquid chromatography Example 1-1

5-(2-Amino-4-methyl-pyrimidin-5-yl)-2-chloro-N-phenyl-benzenesulfonamide

Step 1: 2-Chloro-5-(2-oxo-propyl)-N-phenyl-benzenesulfonamide

Aniline hydrochloride (64.8 mg, 0.05 mmol) is dissolved in 1,4-dioxane (1 ml) in a reaction tube and Na₂CO₃ (85 mg) dissolved in water (0.5 ml) is added. To this mixture is added 2-Chloro-5-(2-oxo-propyl)-benzenesulfonyl chloride (115 mg, 0.43 mmol) (Intermediate A, prepared as described in WO03072557, page 77) in 1,4-dioxane (1 ml). The reaction mixture is left at room temperature overnight and monitored by LC-MS. The reaction mixture is shaken overnight with amino polystyrene (300 mg) and macroporous-isocyanate (300 mg), filtered and the resin is washed with MeOH (0.5 ml). The filtrate is concentrated in vacuo to afford the title compound.

Step 1 Alternative

The transformation may alternatively be carried out using pyridine as solvent.

Step 2: 2-Chloro-5-{1-[1-dimethylamino-meth-(E)-ylidene]-2-oxo-propyl}-N-phenyl-benzenesulfonamide 2-Chloro-5-(2-oxo-propyl)-N-phenyl-benzenesulfonamide (65 mg, 0.20 mmol) is added to a solution of N,N-dimethylformamide dimethyl acetyl (107 ul) in DCM (1 ml). The reaction mixture is shaken at room temperature for 2 hours then concentrated in vacuo to afford the title compound.

Step 3: 5-(2-Amino-4-methyl-pyrimidin-5-yl)-2-chloro-N-phenyl-benzenesulfonamide Guanidine hydrochloride (48 mg, 0.55 mmol) is suspended in 0.55 ml of 1M NaOEt in EtOH and shaken for 10 minutes.

The suspension is filtered and the resulting solution is added to 2-Chloro-5-{1-[1-dimethylamino-meth-(E)-ylidene]-2-oxo-propyl}-N-phenyl-benzenesulfonamide (crude residue from step 2) in 0.5 ml EtOH. The reaction mixture is shaken at room temperature overnight and then evaporated to dryness. Purification of the crude product by preparative LC-MS affords the title compound.

Examples 1-2 to 1-38

These compounds, namely
5-(2-Amino-4-methyl-pyrimidin-5-yl)-2-bromo-N-(2-hydroxy-ethyl)-benzenesulfonamide (Example 1-2)
5-(2-Amino-4-methyl-pyrimidin-5-yl)-2-bromo-N-propyl-benzenesulfonamide (Example 1-3)
5-(2-Amino-4-methyl-pyrimidin-5-yl)-2-bromo-N-(2-hydroxy-ethyl)-N-methyl-benzenesulfonamide (Example 1-4)
5-(2-Amino-4-methyl-pyrimidin-5-yl)-2-chloro-N-methyl-benzenesulfonamide (Example 1-5)
5-(2-Amino-4-methyl-pyrimidin-5-yl)-2-methyl-N-phenyl-benzenesulfonamide (Example 1-6)
5-(2-Amino-4-methyl-pyrimidin-5-yl)-2-fluoro-N-phenyl-benzenesulfonamide (Example 1-7)
5-(2-Amino-4-methyl-pyrimidin-5-yl)-2-bromo-N-(2-methoxy-ethyl)-N-methyl-benzenesulfonamide (Example 1-8)
5-(2-Amino-4-methyl-pyrimidin-5-yl)-2-chloro-N-(2-hydroxy-ethyl)-N-methyl-benzenesulfonamide (Example 1-9)
5-(2-Amino-4-methyl-pyrimidin-5-yl)-2-bromo-N-(2-methoxy-ethyl)-benzenesulfonamide (Example 1-10)
5-(2-Amino-4-methyl-pyrimidin-5-yl)-2-chloro-N-(2-methoxy-ethyl)-benzenesulfonamide (Example 1-11)
5-[4-Chloro-3-(pyrrolidine-1-sulfonyl)-phenyl]-4-methyl-pyrimidin-2-ylamine (Example 1-12)
5-(2-Amino-4-methyl-pyrimidin-5-yl)-N-(2-hydroxy-ethyl)-2-methoxy-benzenesulfonamide (Example 1-13)
5-[4-Bromo-3-(pyrrolidine-1-sulfonyl)-phenyl]-4-methyl-pyrimidin-2-ylamine (Example 1-14)
5-(2-Amino-4-methyl-pyrimidin-5-yl)-2-chloro-N2N-dimethyl-benzenesulfonamide (Example 1-15)
5-(2-Amino-4-methyl-pyrimidin-5-yl)-2-chloro-N-(2-methoxy-ethyl)-N-methyl-benzenesulfonamide (Example 1-16)
5-(2-Amino-4-methyl-pyrimidin-5-yl)-N-(2-hydroxy-ethyl)-2-methyl-benzenesulfonamide (Example 1-17)
5-[4-Bromo-3-(morpholine-4-sulfonyl)-phenyl]-4-methyl-pyrimidin-2-ylamine (Example 1-18)
5-[4-Bromo-3-(4-methyl-piperazine-1-sulfonyl)-phenyl]-4-methyl-pyrimidin-2-ylamine (Example 1-19)
5-(2-Amino-4-methyl-pyrimidin-5-yl)-2-bromo-N-(2-dimethylamino-ethyl)-benzenesulfonamide (Example 1-20)
5-(2-Amino-4-methyl-pyrimidin-5-yl)-2,N,N-trimethyl-benzenesulfonamide (Example 1-21)
5-(2-Amino-4-methyl-pyrimidin-5-yl)-N-(2-cyano-ethyl)-2-methyl-benzenesulfonamide (Example 1-22)
5-[4-Chloro-3-(morpholine-4-sulfonyl)-phenyl]-4-methyl-pyrimidin-2-ylamine (Example 1-23)
5-(2-Amino-4-methyl-pyrimidin-5-yl)-2-fluoro-N-propyl-benzenesulfonamide (Example 1-24)
5-(2-Amino-4-methyl-pyrimidin-5-yl)-N-(2-cyano-ethyl)-2-fluoro-benzenesulfonamide (Example 1-25)
5-(2-Amino-4-methyl-pyrimidin-5-yl)-N-benzyl-2-methyl-benzenesulfonamide (Example 1-26)
5-[4-Chloro-3-(4-methyl-piperazine-1-sulfonyl)-phenyl]-4-methyl-pyrimidin-2-ylamine (Example 1-27)
5-(2-Amino-4-methyl-pyrimidin-5-yl)-2-fluoro-N-(2-methoxy-ethyl)-N-methyl-benzenesulfonamide (Example 1-28)
5-(2-Amino-4-methyl-pyrimidin-5-yl)-2-chloro-N-(2-hydroxy-ethyl)-benzenesulfonamide (Example 1-29)
1-[5-(2-Amino-4-methyl-pyrimidin-5-yl)-2-chloro-benzenesulfonyl]-azetidin-3-ol (Example 1-30)
5-(2-Amino-4-methyl-pyrimidin-5-yl)-2-bromo-N,N-dimethyl-benzenesulfonamide (Example 1-31)
5-[4-Chloro-3-(4-ethyl-piperazine-1-sulfonyl)-phenyl]-4-methyl-pyrimidin-2-ylamine (Example 1-32)
5-[4-Chloro-3-(4-isopropyl-piperazine-1-sulfonyl)-phenyl]-4-methyl-pyrimidin-2-ylamine (Example 1-33)
5-(2-Amino-4-methyl-pyrimidin-5-yl)-2-chloro-N-cyclohexyl-benzenesulfonamide (Example 1-34)
5-(2-Amino-4-methyl-pyrimidin-5-yl)-2-chloro-N-(2-cyano-ethyl)-benzenesulfonamide (Example 1-35)
5-(2-Amino-4-methyl-pyrimidin-5-yl)-2-chloro-N-cyclopentyl-benzenesulfonamide (Example 1-36)
5-(2-Amino-4-methyl-pyrimidin-5-yl)-2-chloro-N-(2-morpholin-4-yl-ethyl)-benzenesulfonamide (Example 1-37)
5-(2-Amino-4-methyl-pyrimidin-5-yl)-N-benzyl-2-chloro-benzenesulfonamide (Example 1-38)
are prepared analogously to Example 1-1 from the appropriate benzenesulfonyl chloride intermediates and commercial amines. The compounds are recovered from reaction mixtures and purified using preparative LC-MS.

Example 1-39

5-(2-Amino-4-methyl-pyrimidin-5-yl)-2-chloro-N-(3-cyano-phenyl)-benzenesulfonamide Step 1: 2-Chloro-N-(3-cyano-phenyl)-5-(2-oxo-propyl)-benzenesulfonamide 3-Aminobenzonitrile (442 mg, 3.7 mmol, 1 eq) is dissolved in dry pyridine (606 ul, 7.5 mmol, 2 eq), under an inert atmosphere of argon. 2-Chloro-5-(2-oxo-propyl)-benzenesulfonyl chloride (Intermediate A)(1.0 g, 3.7 mmol) in 1,4-dioxane (2 ml) is added and the reaction mixture is stirred at room temperature overnight. The solvents are removed in vacuo and the residue is dissolved in DCM and 0.5M HCl. The phases are separated and the organic portion is washed with brine, dried over $MgSO_4$, filtered and concentrated in vacuo to afford the title compound.

Step 2: 2-Chloro-N-(3-cyano-phenyl)-5-{1-[1-dimethylamino-meth-(E)-ylidene]-2-oxo-propyl}-benzenesulfonamide This compound is prepared analogously to Example 1-1 by replacing 2-Chloro-5-(2-oxo-propyl)-N-phenyl-benzenesulfonamide with 2-Chloro-N-(3-cyano-phenyl)-5-(2-oxo-propyl)-benzenesulfonamide and by stirring the reaction mixture at room temperature for 24 hours to afford the title compound.

Step 3: 5-(2-Amino-4-methyl-pyrimidin-5-yl)-2-chloro-N-(3-cyano-phenyl)-benzenesulfonamide This compound is prepared analogously to Example 1-1 by replacing 2-Chloro-5-{1-[1-dimethylamino-meth-(E)-ylidene]-2-oxo-propyl}-N-phenyl-benzenesulfonamide with 2-Chloro-N-(3-cyano-phenyl)-5-{1-[1-dimethylamino-meth-(E)-ylidene]-2-oxo-propyl}-benzenesulfonamide (crude product from step 2). The reaction is carried out at 60°

C. for 24 hours and purification by flash chromatography on silica eluting with 0-10% MeOH:DCM affords the title compound.

Examples 1-40 to 1-48

These compounds, namely
5-(2-Amino-4-methyl-pyrimidin-5-yl)-2-chloro-N-methyl-N-(3-trifluoromethyl-phenyl)-benzenesulfonamide (Example 1-40)
5-(2-Amino-4-methyl-pyrimidin-5-yl)-2-chloro-N-(4-fluoro-3-methyl-phenyl)-benzenesulfonamide (Example 1-41)
5-(2-Amino-4-methyl-pyrimidin-5-yl)-2-chloro-N-(3-trifluoromethyl-phenyl)-benzenesulfonamide (Example 1-42)
5-(2-Amino-4-methyl-pyrimidin-5-yl)-2-chloro-N-(4-chloro-phenyl)-benzenesulfonamide (Example 1-43)
5-(2-Amino-4-methyl-pyrimidin-5-yl)-2-chloro-N-(4-chloro-phenyl)-N-methyl-benzenesulfonamide (Example 1-44)
5-(2-Amino-4-methyl-pyrimidin-5-yl)-2-chloro-N-(3,4-dichloro-phenyl)-N-methyl-benzenesulfonamide (Example 1-45)
5-(2-Amino-4-methyl-pyrimidin-5-yl)-2-chloro-N-methyl-N-phenyl-benzenesulfonamide (Example 1-46)
5-(2-Amino-4-methyl-pyrimidin-5-yl)-N-benzo[1,3]dioxol-5-yl-2-chloro-N-methyl-benzenesulfonamide (Example 1-47)
5-(2-Amino-4-methyl-pyrimidin-5-yl)-2-chloro-N-(3-imidazol-1-yl-phenyl)-benzenesulfonamide (Example 1-48)
are prepared analogously to Example 1-39 from 2-Chloro-5-(2-oxo-propyl)-benzenesulfonyl chloride (Intermediate A) and the appropriate amine/aniline starting material. The reactions are carried out with guanidine addition ranging from 1.1 equivalents to 4.4 equivalents in the appropriate amount of EtOH/NaOEt and reaction temperatures ranging from room temperature to 60° C. The compounds are recovered from reaction mixtures and purified using conventional techniques such as, for example, flash chromatography.

Example 1-49

N-[5-(2-Amino-4-methyl-pyrimidin-5-yl)-2-chloro-phenyl]-methanesulfonamide

Step 1: N-[2-Chloro-5-(2-oxo-propyl)-phenyl]-methanesulfonamide

To a solution of 1-(3-Amino-4-chloro-phenyl)-propan-2-one (Intermediate D) (0.5 g, 2.73 mmol) in DCM (2 ml) and pyridine (1 ml) is added drop wise methanesulfonyl chloride (0.34 g, 0.23 ml, 3.0 mmol) at 0° C. (ice-bath). The reaction mixture is allowed to warm to room temperature and stirred for 3 days. The solvents are removed in vacuo and the residue is dissolved in EtOAc and washed with water, the organic portion is dried over MgSO$_4$, filtered and concentrated in vacuo. Purification of the crude residue by flash chromatography on silica eluting with EtOAc affords the title compound.

Step 2: N-(2-Chloro-5-{1-[1-dimethylamino-meth-(E)-ylidene]-2-oxo-propyl}-phenyl-methanesulfonamide This compound is prepared analogously to Example 1-39 by replacing 2-Chloro-N-(3-cyano-phenyl)-5-(2-oxo-propyl)-benzenesulfonamide with N-[2-Chloro-5-(2-oxo-propyl)-phenyl]-methanesulfonamide (crude product from step 1) to afford the title compound.

Step 3: N-[5-(2-Amino-4-methyl-pyrimidin-5-yl)-2-chloro-phenyl]-methanesulfonamide A solution of guanidine (free base) in EtOH is made up as follows: Guanidine hydrochloride (1 g, 10.5 mmol) is dissolved in EtOH (11 ml) and NaOEt in EtOH (21%, 3M) (3.9 ml, 12 mmol) is added. The reaction mixture is stirred at room temperature for 30 minutes then the mixture is filtered to remove the sodium chloride, resulting in a clear solution.
N-(2-Chloro-5-{1-[1-dimethylamino-meth-(E)-ylidene]-2-oxo-propyl}-phenyl)-methanesulfonamide (crude product from step 2) is dissolved in EtOH (2 ml). The solution of guanidine in EtOH (3.6 ml. 2.4 mmol) is then added and the reaction mixture is heated at 80° C. for 3 hours. The solvents are removed in vacuo and the resulting residue is dissolved in 2M HCl (aq) and washed with EtOAc, the aqueous portion is adjusted to pH6 by the addition of 2M NaOH (aq) and extracted with EtOAc (3×). The combined organic portion is dried over MgSO$_4$, filtered, concentrated in vacuo and the resulting foam is triturated with MeOH to afford the title compound as a white crystalline solid.

Example 1-50

N-[5-(2-Amino-4-methyl-pyrimidin-5-yl)-2-chloro-phenyl]-benzenesulfonamide

N-[2-Chloro-5-(4,4,5,5-tetramethyl-[1,3,2]dioxaborolan-2-yl)-phenyl]-benzenesulfonamide (Intermediate B) (50 mg, 0.13 mmol), 5-Bromo-4-methyl-pyrimidin-2-ylamine (Intermediate C) (26 mg, 0.14 mmol) and PdCl$_2$(dppf).DCM (10 mg, 0.013 mmol) are placed in a microwave vial containing degassed DME (3 ml) and 2M Na$_2$CO$_3$ (1 ml). The resulting mixture is heated using microwave radiation at 100° C. for 45 minutes. The reaction mixture is diluted with DCM, MgSO$_4$ is added and the mixture is filtered through Celite® (filter agent). The filtrate is absorbed onto silica and purification by flash chromatography on silica eluting with MeOH:DCM (1% to 2% MeOH) affords the title compound.

Example 1-51 to 1-53

These compounds, namely
5-(2-Amino-4-methyl-pyrimidin-5-yl)-2-chloro-N-(tetrahydro-pyran-4-yl)-benzenesulfonamide (Example 1-51)
5-(2-Amino-4-methyl-pyrimidin-5-yl)-2-chloro-N-cycloheptyl-benzenesulfonamide (Example 1-52)
1-[5-(2-Amino-4-methyl-pyrimidin-5-yl)-2-chloro-benzenesulfonyl]-piperidin-4-ol (Example 1-53)
are prepared analogously to Example 1-39 from 2-Chloro-5-(2-oxo-propyl)-benzenesulfonyl chloride (Intermediate A) and the appropriate amine/piperidine starting material. The compounds are recovered from reaction mixtures and purified using conventional techniques such as, for example, flash chromatography.

Example 1-54

5-(2-Amino-4-methyl-pyrimidin-5-yl)-N-benzo[1,3]dioxol-5-yl-2-chloro-benzenesulfonamide Step 1: N-Benzo[1,3]dioxol-5-yl-2-chloro-5-(2-oxo-propyl)-benzenesulfonamide This compound is prepared analogously to Example 1-39 by replacing 3-aminobenzonitrile with 3,4-(methylenedioxy)

aniline. Purification of the crude residue by flash chromatography on silica eluting with EtOAc/iso-hexanes (30%) affords the title compound.

Step 2: N-Benzo[1,3]dioxol-5-yl-2-chloro-5-{1-[1-dimethylamino-meth-(E)-ylidene]-2-oxo-propyl}-benzenesulfonamide This compound is prepared analogously to Example 1-39 by replacing 2-Chloro-N-(3-cyano-phenyl)-5-(2-oxo-propyl)-benzenesulfonamide with N-Benzo[1,3]dioxol-5-yl-2-chloro-5-(2-oxo-propyl)-benzenesulfonamide and by replacing N,N-dimethylformamide dimethyl acetyl with t-butoxy-bis(dimethylamino) methane to afford the title compound.

Step 3: 5-(2-Amino-4-methyl-pyrimidin S-yl)-N-benzo[1,3]dioxol-5-yl-2-chloro-benzenesulfonamide This compound is prepared analogously to Example 1-39 by replacing 2-Chloro-N-(3-cyano-phenyl)-5-{1-[1-dimethylamino-meth-(E)-ylidene]-2-oxo-propyl}-benzene sulfonamide with N-Benzo[1,3]dioxol-5-yl-2-chloro-5-{1-[1-dimethylamino-meth-(E)-ylidene]-2-oxo-propyl}-benzenesulfonamide to afford the title compound.

Example 1-55

5-(2-Amino-4-methyl-pyrimidin-5-yl)-2-chloro-N-pyridin-3-yl-benzenesulfonamide

This compound is prepared analogously to Example 1-54 by replacing 3,4-(methylenedioxy)aniline in step 1 with 3-aminopyridine to afford the titled compound.

Example 2-1

2-tert-Butyl-4'-methyl-[4,5']bipyrimidinyl-2'-ylamine

Step 1: 1-(2-tert-Butyl-pyrimidin-4-yl)-propan-2-one

This compound is prepared as described in WO2004096797.

Step 2: 2-tert-Butyl-4'-methyl-[4,5']bipyrimidinyl-2'-ylamine

This compound is prepared analogously to Example 1-1 (steps 2 & 3) by replacing 1-[4-chloro-3-(4-methyl-piperazine-1-sulfonyl)-phenyl]-propan-2-one with 1-(2-tert-Butyl-pyrimidin-4-yl)-propan-2-one to afford the title compound.

Examples 3-1 to 3-17

These compounds, namely
5-(2-Amino-4-methyl-pyrimidin-5-yl)-2-chloro-N-cyclopropyl-benzenesulfonamide (Example 3-1)
5-(2-Amino-4-methyl-pyrimidin-5-yl)-2-chloro-N-cyclobutyl-benzenesulfonamide (Example 3-2)
5-[3-(Azetidine-1-sulfonyl)-4-chloro-phenyl]-4-methyl-pyrimidin-2-ylamine (Example 3-3)
5-(2-Amino-4-methyl-pyrimidin-5-yl)-N-bicyclo[3.2.1]oct-3-yl-2-chloro-benzenesulfonamide (Example 3-4)
5-(2-Amino-4-methyl-pyrimidin-5-yl)-2-chloro-N-((1R,2R)-2-hydroxy-cyclohexyl)benzenesulfonamide (Example 3-5)
5-(2-Amino-4-methyl-pyrimidin-5-yl)-2-chloro-N-(4,4-difluoro-cyclohexyl)-benzenesulfonamide (Example 3-6)
5-(2-Amino-4-methyl-pyrimidin-5-yl)-2-chloro-N-(5-hydroxy-adamantan-2-yl)-benzenesulfonamide (Example 3-7)
5-(2-Amino-4-methyl-pyrimidin-5-yl)-2-chloro-N-(3-hydroxy-adamantan-1-yl)-benzenesulfonamide (Example 3-8)
5-(2-Amino-4-methyl-pyrimidin-5-yl)-2-chloro-N-(2,2-dimethyl-propyl)-benzenesulfonamide (Example 3-9)
5-(2-Amino-4-methyl-pyrimidin-5-yl)-2-chloro-N-(2-pyridin-4-yl-ethyl)-benzenesulfonamide (Example 3-10)
5-(2-Amino-4-methyl-pyrimidin-5-yl)-2-chloro-N-(3-pyridin-3-yl-propyl)-benzenesulfonamide (Example 3-11)
5-(2-Amino-4-methyl-pyrimidin-5-yl)-2-chloro-N-(4-pyridin-3-yl-butyl)-benzenesulfonamide (Example 3-12)
5-(2-Amino-4-methyl-pyrimidin-5-yl)-N-pyridin-2-yl-2-chloro-benzenesulfonamide (Example 3-13)
5-(2-Amino-4-methyl-pyrimidin-5-yl)-N-pyridin-4-yl-2-chloro-benzenesulfonamide (Example 3-14)
trans-{4-[5-(2-Amino-4-methyl-pyrimidin-5-yl)-2-chloro-benzenesulfonylamino]-cyclohexylmethyl}-carbamic acid tert-butyl ester (Example 3-15)
trans-{4-[5-(2-Amino-4-methyl-pyrimidin-5-yl)-2-chloro-benzenesulfonylamino]-cyclohexyl}-carbamic acid tert-butyl ester (Example 3-16)
cis-{4-[5-(2-Amino-4-methyl-pyrimidin-5-yl)-2-chloro-benzenesulfonylamino]-cyclohexyl}-carbamic acid tert-butyl ester (Example 3-17)
are prepared analogously to Example 1-1 from the appropriate benzenesulfonyl chloride intermediates and amines. The compounds are recovered from reaction mixtures and purified using conventional techniques such as, for example, flash chromatography.

Example 3-18

N-(4-Aminomethyl-cyclohexyl)-5-(2-amino-4-methyl-pyrimidin-5-yl)-2-chloro-benzenesulfonamide 4M HCl in dioxane (1.2 ml) is added to a stirred solution of {4-[5-(2-amino-4-methyl-pyrimidin-5-yl)-2-chloro-benzenesulfonylamino]-cyclohexylmethyl}-carbamic acid tert-butyl ester (Example 3-17) (0.25 g, 0.49 mmol) in dioxane (1 ml). After 18 h the solvent is removed to give the title compound.

Examples 3-19 to 3-21

These compounds, namely
5-(2-Amino-4-methyl-pyrimidin-5-yl)-2-chloro-N-piperidin-4-yl-benzenesulfonamide (Example 3-19)
trans-N-(4-Amino-cyclohexyl)-5-(2-amino-4-methyl-pyrimidin-5-yl)-2-chloro-benzenesulfonamide (Example 3-20)
cis-N-(4-Amino-cyclohexyl)-5-(2-amino-4-methyl-pyrimidin-5-yl)-2-chloro-benzenesulfonamide (Example 3-21)
are prepared analogously to Example 3-18 from the appropriate BOC protected amines. The compounds are recovered from reaction mixtures and purified using conventional techniques such as, for example, flash chromatography.

Example 3-22

N-{4-[5-(2-Amino-4-methyl-pyrimidin-5-yl)-2-chloro-benzenesulfonylamino]-cyclohexylmethyl}-acetamide Acetyl chloride (0.045 ml, 0.066 mmol) is added to a stirred solution of N-(4-aminomethyl-cyclohexyl)-5-(2- amino-4-methyl-pyrimidin-5-yl)-2-chloro-benzenesulfonamide (Example 3-18) (0.090 g, 0.22 mmol) in dry pyridine (1 ml). After 30 min the reaction mixture is absorbed on silica and the product is purified by chromatography on silica, eluting with ethyl acetate to afford the title compound.

Examples 3-23 to 3-25

These compounds, namely
N-(1-Acetyl-piperidin-4-yl)-5-(2-amino-4-methyl-pyrimidin-5-yl)-2-chloro-benzenesulfonamide (Example 3-23)
trans-N-{4-[5-(2-Amino-4-methyl-pyrimidin-5-yl)-2-chloro-benzenesulfonylamino]-cyclohexyl}-acetamide (Example 3-24)
cis-N-{4-[5-(2-Amino-4-methyl-pyrimidin-5-yl)-2-chloro-benzenesulfonylamino]-cyclohexyl}-acetamide (Example 3-25)
are prepared analogously to Example 3-22 from the appropriate amines (Examples 3-19, 3-20, 3-21). The compounds are recovered from reaction mixtures and purified using conventional techniques such as, for example, flash chromatography.

Example 3-26

5-(2-Amino-4-methyl-pyrimidin-5-yl)-2-chloro-N-(4-hydroxy-cyclohexyl)-benzenesulfonamide Step 1: 5-Bromo-2-chloro-N-(4-hydroxy-cyclohexyl)-benzenesulfonamide 5-Bromo-2-chloro-benzenesulfonyl chloride (1.0 g, 3.45 mmol) (Intermediate E, Step 1) and pyridine (2 ml) are added to a stirred suspension of trans-4-aminocyclohexanol (2.0 g, 17.2 mmol) suspended in DCM (20 ml). After 18 h, the solvents are removed and the residue is partitioned between aq. 1M HCl and ethyl acetate. The organic extract is dried over $Mg_2SO_4$ and the solvent is removed. The residue is purified by chromatography on silica, eluting with ethyl acetate:hexane (1:1 to 1:0) to give the title compound.

Step 2: 2-Chloro-N-(4-hydroxy-cyclohexyl)-5-(4,4,5,5-tetramethyl-[1,3,2]dioxaborolan-2-yl)-benzenesulfonamide Nitrogen is bubbled through a stirred mixture of 5-bromo-2-chloro-N-(4-hydroxy-cyclohexyl)-benzenesulfonamide (0.832 g, 2.26 mmol), bis(pinacolato)diborane (0.63 g, 2.48 mmol) and potassium acetate (0.332 g, 3.39 mmol) in DME (15 ml) for 15 min. $PdCl_2$(dppf). DCM (0.184 g, 0.23 mmol) is added and the reaction is stirred at 90° C. for 18 h under nitrogen. The reaction is allowed to cool then diluted with ethyl acetate, filtered through a Celite® pad (filter agent) and concentrated. The residue is dissolved in ethyl acetate and washed with water, followed by brine, and dried ($MgSO_4$). The solvent is removed to give the title compound (1.48 g) which is used crude in the next step.

Step 3: 5-(2-Amino-4-methyl-pyrimidin-5-yl)-2-chloro-N-(4-hydroxy-cyclohexyl)-Benzenesulfonamide The crude 2-chloro-N-(4-hydroxy-cyclohexyl)-5-(4,4,5,5-tetramethyl-[1,3,2]dioxaborolan-2-yl)-benzenesulfonamide from step 2 (1.48 g), 5-Bromo-4 methyl-pyrimidin-2-ylamine (intermediate C) (0.669 g, 3.36 mmol) and $PdCl_2$(dppf).DCM (0.436 g, 0.53 mmol) are placed in a microwave vial containing degassed DME (10 ml) and 2M $Na_2CO_3$ (2 ml). The resulting mixture is heated using microwave radiation at 100° C. for 15 minutes. After evaporation of the solvent, the reaction mixture is purified by flash chromatography on silica eluting with ethanol to afford the title compound.

Example 3-27

5-(2-Amino-4-methyl-pyrimidin-5-yl)-2-chloro-N-(5-trifluoromethyl-pyridin-2-yl)-benzenesulfonamide Step 1: 5-Bromo-2-chloro-N-(5-trifluoromethyl-pyridin-2-yl)-benzenesulfonamide The titled compound is prepared as described for 5-Bromo-2-chloro-N-phenyl-benzenesulfonamide (Intermediate F, step 2), by replacing aniline in this procedure with 5-trifluoromethyl-pyridin-2-ylamine Step 2: 5-(2-Amino-4-methyl-pyrimidin-5-yl)-2-chloro-N-(5-trifluoromethyl-pyridin-2-yl)benzenesulfonamide A 5 ml microwave tube is charged with 5-bromo-2-chloro-N-(5-trifluoromethyl-pyridin-2-yl)-benzenesulfonamide (0.067 g, 0.16 mmol) and DME (degassed 3 ml), 4-methyl-5-(4,4,5,5-tetramethyl-[1,3,2]dioxaborolan-2-yl]-pyrimidin-2-ylamine (Intermediate G) (0.0535 g, 0.19 mmol), 2 M aqueous $Na_2CO_3$ solution (640 µl) and $PdCl_2$(dppf).DCM (0.00448 g, 5.4 µmol) and the mixture is heated using microwave radiation at 110° C. for 15 min. After cooling to room temperature the mixture is taken up in ethyl acetate (50 ml), washed with water, dried over $MgSO_4$ and concentrated in vacuo. The crude product is triturated with DCM (0.5 ml), filtrated and washed with DCM to afford the pure title compound.

Examples 3-28 to 3-33

These compounds, namely
5-(2-Amino-4-methyl-pyrimidin-5-yl)-2-chloro-N-(6-methyl-pyridin-2-yl)-benzenesulfonamide (Example 3-28)
5-(2-Amino-4-methyl-pyrimidin-5-yl)-2-chloro-N-(5-cyano-pyridin-2-yl)-benzenesulfonamide (Example 3-29)
5-(2-Amino-4-methyl-pyrimidin-5-yl)-2-chloro-N-(3-methyl-pyridin-2-yl)-benzenesulfonamide (Example 3-30)
5-(2-Amino-4-methyl-pyrimidin-5-yl)-2-chloro-N-(5-fluoro-pyridin-2-yl)-benzenesulfonamide (Example 3-31)
5-(2-Amino-4-methyl-pyrimidin-5-yl)-2-chloro-N-(5-chloro-pyridin-2-yl)-benzenesulfonamide (Example 3-32)
5-(2-Amino-4-methyl-pyrimidin-5-yl)-2-chloro-N-(6-cyano-pyridin-3-yl)-benzenesulfonamide (Example 3-33)
are prepared by a similar procedure to Example 3-27 using the appropriate amine in the first step.

Examples 3-34

Pyridine-3-sulfonic acid [5-(2-amino-4-methyl-pyrimidin-5-yl)-2-chlorophenyl]-amide Step 1: Pyridine-3-sulfonic acid [5-bromo-2-chloro-phenyl]-amide This compound is prepared analogously to Intermediate E (step 2), by replacing 5-bromo-2-chloro-benzenesulfonyl chloride in this procedure with pyridine-3-sulfonyl chloride and aniline with S-bromo-2-chloroaniline to afford the title compound.

Step 2: Pyridine-3-sulfonic acid [5-(2-amino-4-methyl-pyrimidin-5-yl)-2-chlorophenyl]-amide This compound is prepared as described for Example 3-25 (step 2) from 4-Methyl-5-(4,4,5,5-tetramethyl-[1,3,2]dioxaborolan-2-yl]-pyrimidin-2-ylamine (Intermediate G) and pyridine-3-sulfonic acid [5-bromo-2-chloro-phenyl]-amide.

Examples 3-35

N-[5-(2-Amino-4-methyl-pyrimidin-5-yl)-2-chlorophenyl]-3-chloro-benzene sulfonamide This compound is prepared by an analogous procedure to Example 3-34, substituting pyridine-3-sulfonyl chloride by 3-chloro-benzenesulfonyl chloride in the first step.

Examples 3-36

5-(2-Amino-4-methyl-pyrimidin-5-yl)-N-phenyl-2-trifluoromethyl-benzene sulphonamide This compound is prepared analogously to Example 3-26 by replacing 2-chloro-N-(4-hydroxy-cyclohexyl)-5-(4,4,5,5-tetramethyl-[1,3,2]dioxaborolan-2-yl)-benzenesulfonamide, in step 3, with 2-trifluoromethyl-N-phenyl-5-(4,4,5,5-tetramethyl-[1,3,2]dioxaborolan-2-yl)-benzenesulfonamide (Intermediate F) and by changing the reaction temperature/time to 120° C./15 min.

Examples 3-37

5-(2-Amino-4-methyl-pyrimidin-5-yl)-N-benzo[1,3]dioxol-5-yl-2-trifluoro methyl-benzenesulfonamide Step 1: N-Benzo[1,3]dioxol-5-yl-5-chloro-2-trifluoromethyl-benzenesulfonamide This compound is prepared analogously to Intermediate E (step 2) by replacing S-bromo-2-chloro-benzenesulfonyl chloride with 5-chloro-2-trifluoromethyl-benzenesulfonyl chloride and by replacing aniline with 3,4-(methylenedioxy) aniline to afford the title compound.

Step 2: 5-(2-Amino-4-methyl-pyrimidin-5-yl)-N-benzo[1,3]dioxol-5-yl-2-trifluoromethyl-benzenesulfonamide N-Benzo[1,3]dioxol-5-yl-5-chloro-2-trifluoromethyl-benzenesulfonamide (0.088 g, 0.23 mmol), 4-methyl-5-(4,4,5,5-tetramethyl-[1,3,2]dioxaborolan-2-yl)-pyrimidin-2-ylamine (Intermediate G, prepared according to WO 2007/084786, p. 92) (0.082 g, 0.34 mmol) and PdCl$_2$(dppf).DCM (0.0185 g, 0.023 mmol) are placed in a microwave vial containing degassed DME (2 ml) and 2M Na$_2$CO$_3$ (0.23 ml). The resulting mixture is heated using microwave radiation at 120° C. for 60 minutes. After evaporation of the solvent, the reaction mixture is purified by flash chromatography on silica eluting with cyclohexane/EtOAc (1:2) to afford the title compound.

Examples 3-38 to 3-56

These compounds, namely
5-(2-Amino-4-methyl-pyrimidin-5-yl)-N-(2,2-difluoro-benzo[1,3]dioxol-5-yl)-2-trifluoromethyl-benzene-sulfonamide (Example 3-38)
5-(2-Amino-4-methyl-pyrimidin-5-yl)-N-(trans-4-hydro-cyclohexyl)-2-trifluoromethyl-benzenesulfonamide (Example 3-39)
5-(2-Amino-4-methyl-pyrimidin-5-yl)-N-(6-methyl-pyridin-2-yl)-2-trifluoromethyl-benzenesulfonamide (Example 3-40)
5-(2-Amino-4-methyl-pyrimidin-5-yl)-N-(3,4-dimethyl-phenyl)-2-trifluoromethyl-benzenesulfonamide (Example 3-41)
5-(2-Amino-4-methyl-pyrimidin-5-yl)-N-(3,4-dimethoxy-phenyl)-2-trifluoromethyl-benzenesulfonamide (Example 3-42)
5-(2-Amino-4-methyl-pyrimidin-5-yl)-N-[trans-4-(methanesulfonylamino-methyl)-cyclohexyl]-2-trifluoromethyl-benzenesulfonamide (Example 3-43)
5-(2-Amino-4-methyl-pyrimidin-5-yl)-N-{trans-4-[N,N-(dimethylamino)-sulfonylamino-methyl]-cyclohexyl}-2-trifluoromethyl-benzenesulfonamide (Example 3-44)
5-(2-Amino-4-methyl-pyrimidin-5-yl)-N-(trans-4-hydroxymethyl-cyclohexyl)-2-trifluoromethyl-benzenesulfonamide (Example 3-45)
trans-4-[5-(2-Amino-4-methyl-pyrimidin-5-yl)-2-trifluoromethyl-benzenesulfonylamino]-cyclohexanecarboxylic acid methyl ester (Example 3-46)
5-(2-Amino-4-methyl-pyrimidin-5-yl)-N-(2-hydroxy-cyclohexyl)-2-trifluoromethyl-benzenesulfonamide (Example 3-47)
5-(2-Amino-4-methyl-pyrimidin-5-yl)-N-(cis-4-hydroxy-cyclohexyl)-2-trifluoromethyl-benzenesulfonamide (Example 3-48)
{trans-4-[5-(2-Amino-4-methyl-pyrimidin-5-yl)-2-trifluoromethyl-benzenesulfonylamino]-cyclohexyl}-carbamic acid tert-butyl ester (Example 3-49)
5-(2-Amino-4-methyl-pyrimidin-5-yl)-N-((1S,2R)-2-hydroxy-cyclopentyl)-2-trifluoromethyl-benzenesulfonamide (Example 3-50)
5-(2-Amino-4-methyl-pyrimidin-5-yl)-N-(4-tert-butyl-cyclohexyl)-2-trifluoromethyl-benzenesulfonamide (Example 3-51)
5-(2-Amino-4-methyl-pyrimidin-5-yl)-N-((1S,2S)-2-hydroxy-cyclohexyl)-2-trifluoromethyl-benzenesulfonamide (Example 3-52)
5-(2-Amino-4-methyl-pyrimidin-5-yl)-N-((1R,2S)-2-hydroxy-cyclohexyl)-2-trifluoromethyl-benzenesulfonamide (Example 3-53)
5-(2-Amino-4-methyl-pyrimidin-5-yl)-2-trifluoromethyl-N-(1,3,5-trimethyl-1H-pyrazol-4-ylmethyl)-benzenesulfonamide (Example 3-54)
5-(2-Amino-4-methyl-pyrimidin-5-yl)-N-(cis-4-hydroxymethyl-cyclohexyl)-2-trifluoromethyl-benzenesulfonamide (Example 3-55)
5-(2-Amino-4-methyl-pyrimidin-5-yl)-N-((1R,2S)-2-hydroxy-cyclohexyl)-2-trifluoromethyl-benzenesulfonamide (Example 3-56)
are prepared analogously to Example 4 from 5-chloro-2-trifluoromethyl-benzenesulfonyl chloride and appropriate amines. Crude products are all purified by flash chromatography on silica or by preparative HPLC on reversed phase or by a combination of both.

Examples 3-57

5-(2-Amino-4-methyl-pyrimidin-5-yl)-2-chloro-N-(3-hydroxy-cyclohexyl)-benzene sulphonamide This compound is prepared by an analogously to Example 3-26 by replacing trans-4-aminocyclohexanol (step 1) with 3-amino-cyclohexanol.

Preparation of Intermediates

Intermediate A

2-Chloro-5-(2-oxo-propyl)-benzenesulfonyl Chloride

Prepared as described in WO03072557, page 77.

Intermediate B

N-[2-Chloro-5-(4,4,5,5-tetramethyl-[1,3,2]dioxaborolan-2-yl)-phenyl]-benzenesulfonamide Step 1: N-(5-Bromo-2-chloro-phenyl)-benzenesulfonamide To a stirring solution of 5-Bromo-2-chloroaniline (100 mg, 0.48 mmol) in DCM (5 ml) is added benzenesulfonyl chloride (280 mg, 202 ul, 1.58 mmol) and pyridine (195 ul, 2.42 mmol). The reaction mixture is stirred at room temperature for 18 hours. EtOAc (20 ml) is added and the reaction mixture is washed with 0.1 m HCl (20 ml), the phases are separated and the organic portion is washed with water (3×), dried over $MgSO_4$, concentrated in vacuo and dried in a vacuum oven to afford the title compound.

Step 2: N-[2-Chloro-5-(4,4,5,5-tetramethyl-[1,3,2]dioxaborolan-2-yl)-phenyl]-benzenesulfonamide To a stirring solution of N-(5-Bromo-2-chloro-phenyl)-benzenesulfonamide (200 mg, 0.58 mmol) in DME (degassed, 5 ml) is added bis(pinacolato) diboron (158 mg, 0.62), KOAc (47 mg, 0.58 mmol) and $PdCl_2(dppf).DCM$ (69 mg, 0.084 mmol). The reaction mixture is heated at 105° C. overnight. After cooling to room temperature the crude residue is pre-absorbed onto silica and purification by flash chromatography on silica eluting with iso-hexanes/EtOAc (3:1 to 1:1) affords the title compound.

Intermediate C

5-Bromo-4 methyl-pyrimidin-2-ylamine

2-Amino-4-methylpyrimidine (10 g, 91.6 mmol), n-bromosuccinimide (17.9 g, 100.8 mmol) and $CHCl_3$ are mixed together and stirred at room temperature for 1 hour. The solvent is removed in vacuo, water is added and the mixture is stirred at room temperature for 30 minutes. The resulting precipitate is collected by filtration and dried under vacuum oven to afford the title compound.

Intermediate D

1-(3-Amino-4-chloro-phenyl)-propan-2-one

Step 1: 1-Chloro-2-nitro-4-((E)-2-nitro-propenyl)-benzene

A stirred mixture of 3-Nitro-4-chlorobenzaldehyde (10 g, 53.89 mmol), ammonium acetate (1.39 g, 18 mmol) and nitroethane (31.3 ml, 432 mmol) is heated at reflux (80° C.) overnight. After cooling to room temperature the reaction mixture is concentrated if vacuo to give a solid which is dissolved in DCM (200 ml) and washed with water (3×200 ml), followed by brine (200 ml). The organic portion is dried over $MgSO_4$, filtered and concentrated in vacuo to afford the title compound as an orange solid.

Step 2: 1-(3-Amino-4-chloro-phenyl)-propan-2-one

A solution of 1-Chloro-2-nitro-4-((E)-2-nitro-propenyl)-benzene (13.6 g, 56 mmol) in glacial acetic acid (100 ml) is added slowly to a stirred slurry of Iron powder (34 g, 610 mmol) in glacial acetic acid (100 ml) at 60° C. The reaction mixture is stirred at 60° C. for 1 hour then allowed to cool to room temperature and stirred overnight. The reaction mixture is poured onto ice-water (300 ml) and filtered through Celite® (filter agent) washing with DCM (500 ml). The organic portion is separated and washed with water (2×300 ml) and brine (300 ml), dried over $MgSO_4$, filtered and concentrated in vacuo to give a brown oil. The crude residue is absorbed onto silica and purification by flash chromatography on silica eluting with 20% EtOAc/Hexanes affords the title compound.

Intermediate E

2-Chloro-N-phenyl-5-(4,4,5,5-tetramethyl-[1,3,2]dioxaborolan-2-yl)-benzenesulfonamide Step 1: 5-Bromo-2-chloro-benzenesulfonyl chloride To a stirring solution of 2-chloro-5-bromoaniline (2 g, 9.69 mmol) in glacial acetic acid (60 ml) and conc. HCl (20 ml) at 0° C. is added sodium nitrite (668 mg, 9.69 mmol) in water (8 ml). The reaction mixture is stirred at room temperature for 3 hours and then added to a solution of $SO_2/AcOH/CuCl_2/H_2O$ (150 ml) and stirred at room temperature for 18 hours. The reaction mixture is poured into water (800 ml) and extracted with ethyl acetate (3×100 ml). The combined organic layers are washed with water and dried over $MgSO_4$. After filtration the solvent is removed in vacuo to afford the title compound. Preparation of the Reagent $SO_2/AcOH/CuCl_2/H_2O$:

According to the reported procedure (E. E. Gilbert, Synthesis 1969, 1-10, p 6), glacial acetic acid (100 ml) vigorously stirred at room temperature is treated by bubbling $SO_2$ gas. Once a saturated solution is achieved (approximately 10 g per 100 ml), the solution is treated with copper (II) chloride (4 g) in water (5 ml). The resulting mixture is allowed to settle to give a green solution.

Step 2: 5-Bromo-2-chloro-N-phenyl-benzenesulfonamide

To a stirring solution of aniline (0.324 ml, 3.55 mmol) in DCM (10 ml) is added pyridine (1.44 ml, 17.76 mmol) followed by a solution of 5-bromo-2-chloro-benzenesulfonyl chloride (1.03 g, 3.55 mmol) in DCM (10 ml). The reaction mixture is stirred at room temperature for 18 hours. DCM (20 ml) is added and the reaction mixture is washed with 2M HCl (50 ml), dried over $MgSO_4$ and concentrated in vacuo to afford the title compound.

Step 3: 2-Chloro-N-phenyl-5-(4,4,5,5-tetramethyl-[1,3,2]dioxaborolan-2-yl)-benzenesulfonamide To a mixture comprising 5-bromo-2-chloro-N-phenyl-benzenesulfonamide (453 mg, 1.31 mmol), bis(pinacolato)

diboron (365 mg, 1.44 mmol), KOAc (192 mg, 1.97 mmol) and PdCl$_2$(dppf).DCM (107 mg, 0.13 mmol) in DME (degassed, 10 ml) is heated at 90° C. overnight. After cooling to room temperature the reaction mixture is pre-absorbed onto silica and purification by flash chromatography eluting with MeOH/DCM (1:99) affords the title compound.

Intermediate F

2-Trifluoromethyl-N-phenyl-5-(4,4,5,5-tetramethyl-[1,3,2]dioxaborolan-2-yl)benzenesulfonamide This compound is prepared analogously to Intermediate E by replacing 5-bromo-2-chloro-phenylamine in step 1 by 5-chloro-2-trifluoromethylaniline and by changing the reaction temperature/time in step 3 to 100° C./2 h.

Intermediate G

4-Methyl-5-(4,4,5,5-tetramethyl-[1,3,2]dioxaborolan-2-yl]-pyrimidin-2-ylamine

Palladium II dichloride (0.189 g, 1.06 mmol) is added to a solution of [1,1-bis(diphenylphosphino)ferrocene] (0.608 g, 1.06 mmol) in degassed dimethylformamide (20 ml) and the mixture is stirred at 50° C. for 15 min. After cooling to room temperature 5-bromo-4-methylpyrimidine-2-ylamine (1.0 g, 5.32 mmol), bis-(4,4,5,5-tetramethyl-[1,3]dioxolan-2-yl]-borane (1.65 g, 6.38 mmol) and potassium acetate (1.57 g, 16 mmol) are added. The mixture is heated at 95° C. for 16 hours then the solvent is removed under reduced pressure. The crude mixture is suspended in DCM (250 ml) and filtered through a pad of Celite® (filter agent), the filtrate was washed with water (20 ml), dried over MgSO$_4$ and evaporated to dryness. Purification by flash chromatography on silica using cyclohexane/ethyl acetate (4:1) mixture provides the title compounds.

We claim:

1. A compound of formula I

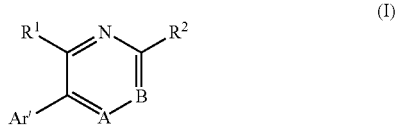

(I)

or a pharmaceutically acceptable salt, wherein:
$R^1$ is hydrogen;
$R^2$ is amino;
A is $CR^3$;
B is N;
Ar' is

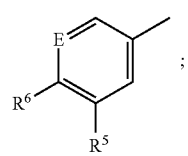

E is CH or N;
$R^3$ is hydrogen, $C_1$-$C_6$-alkyl, $C_1$-$C_6$-haloalkyl, $C_4$-$C_8$ carbocyclyl, a 5-8 membered heterocyclyl or a group —Y—Z, where said rings are optionally substituted by one or more substituents selected from List X;

Y is a direct link, —O—(CH$_2$)$_n$— or —N(R$^4$)—(CH$_2$)$_o$—;
Z is phenyl or a 5-6 membered heteroaryl, where said rings are optionally substituted by one or more substituents selected from List X;
$R^4$ is hydrogen or $C_1$-$C_6$-alkyl;
$R^5$ is SO$_2$NR$^7$R$^8$ or NR$^9$SO$_2$R$^{10}$;
$R^6$ is hydrogen, halo, hydroxyl, cyano, $C_1$-$C_3$-alkyl, $C_1$-$C_3$-haloalkyl, $C_1$-$C_3$-alkoxy or $C_1$-$C_3$-haloalkoxy; or $R^5$ and $R^6$ together form a 5-6 membered heteroaryl or 5-8 membered heterocyclyl, where each ring is optionally substituted by one or more substituents selected from List X;
$R^7$, $R^9$, $R^{11}$, $R^{13}$ and $R^{15}$ are independently hydrogen or $C_1$-$C_6$-alkyl;
$R^8$, $R^{10}$, $R^{12}$, $R^{14}$ and $R^{16}$ are independently hydrogen, $C_1$-$C_6$-alkyl or —(CH$_2$)$_p$—R$^{17}$, or $R^{10}$ and $R^{12}$ are additionally independently $C_1$-$C_6$-alkoxy, where said alkyl and alkoxy groups may be substituted by one to five halo or by hydroxyl, $C_1$-$C_6$-alkoxy, NR$^{18}$R$^{19}$ or CN;
$R^{17}$ is $C_6$-$C_{14}$-aryl, 5-10 membered heteroaryl, $C_4$-$C_8$ carbocyclyl, a 4-8 membered heterocyclyl, a $C_6$-$C_{14}$-aryl fused with a $C_4$-$C_8$ carbocyclyl or a 4-8 membered heterocyclyl, or a 5-10 membered heteroaryl fused with a $C_4$-$C_8$ carbocyclyl or a 4-8 membered heterocyclyl, where said rings are optionally substituted by one or more substituents selected from List X;
or $R^7$ and $R^8$, $R^{13}$ and $R^{14}$ or $R^{15}$ and $R^{16}$ may form a 4-8 membered heterocyclyl containing at least one N ring atom, where said ring is optionally substituted by halo, hydroxyl, $C_1$-$C_6$-alkyl, $C_1$-$C_6$-haloalkyl, $C_1$-$C_6$-alkoxy or $C_1$-$C_6$-haloalkoxy or cyano;
$R^{18}$ and $R^{19}$ are independently hydrogen or $C_1$-$C_6$-alkyl;
n is an integer from 0 to 2, o is an integer from 0 to 2 and p is an integer from 0 to 2;
List X is represented by hydroxyl, cyano, nitro, $C_1$-$C_6$-alkyl, $C_2$-$C_6$-alkenyl, $C_2$-$C_6$-alkynyl, $C_1$-$C_6$-alkoxy, $C_1$-$C_6$-alkenyloxy, $C_2$-$C_6$-alkynyloxy, —O—($C_1$-$C_4$-alkylene)-R$^{20}$, —O—($C_2$-$C_4$-alkylene)-R$^{21}$, halogen, $C_1$-$C_6$-alkylcarbonyl, carboxy, $C_1$-$C_6$-alkoxycarbonyl, amino, $C_1$-$C_6$-alkylamino, di-$C_1$-$C_6$-alkylamino, $C_1$-$C_6$-alkylaminocarbonyl, di-$C_1$-$C_6$-alkylaminocarbonyl, $C_1$-$C_6$-alkylcarbonylamino, $C_1$-$C_6$-alkylcarbonyl($C_1$-$C_6$-alkyl)amino, $C_1$-$C_6$-alkylsulfonylamino, $C_1$-$C_6$-alkylsulfonyl($C_1$-$C_6$-alkyl)amino, $C_1$-$C_6$-thioalkyl, $C_1$-$C_6$-alkylsulfinyl, $C_1$-$C_6$-alkylsulfonyl, aminosulfonyl, $C_1$-$C_6$-alkylaminosulfonyl, di-$C_1$-$C_6$-alkylaminosulfonyl, phenyl or 5-6 membered heteroaryl, where each of the afore-mentioned hydrocarbon groups may be optionally substituted by one or more halogen, hydroxyl, $C_1$-$C_6$-alkoxy, amino, $C_1$-$C_6$-alkylamino, di-$C_1$-$C_6$-alkylamino or cyano, and where said phenyl or heteroaryl group may be optionally substituted by one or more groups selected from hydroxyl, cyano, nitro, $C_1$-$C_6$-alkyl, $C_1$-$C_6$-haloalkyl, $C_1$-$C_6$-alkenyl, $C_1$-$C_6$-alkynyl, $C_1$-$C_6$-alkoxy, $C_1$-$C_6$-alkenyloxy, $C_1$-$C_6$-alkynyloxy, halogen, $C_1$-$C_6$-alkylcarbonyl, carboxy, $C_1$-$C_6$-alkoxycarbonyl, amino, $C_1$-$C_6$-alkylamino, di-$C_1$-$C_6$-alkylamino, $C_1$-$C_6$-alkylaminocarbonyl, di-$C_1$-$C_6$-alkylaminocarbonyl, $C_1$-$C_6$-alkylcarbonylamino, $C_1$-$C_6$-alkylcarbonyl($C_1$-$C_6$-alkyl)amino, $C_1$-$C_6$-alkylsulfonylamino, $C_1$-$C_6$-alkylsulfonyl($C_1$-$C_6$-alkyl)amino, $C_1$-$C_6$-thioalkyl, $C_1$-$C_6$-alkylsulfinyl, $C_1$-$C_6$-alkylsulfonyl, aminosulfonyl, $C_1$-$C_6$-alkylaminosulfonyl or di-$C_1$-$C_6$-alkylaminosulfonyl groups;

$R^{20}$ represents $C_2$-$C_4$-alkenyl, $C_2$-$C_4$-alkynyl, halogen, cyano, nitro, $C_1$-$C_6$-alkylcarbonyl, carboxy, $C_1$-$C_6$-alkoxycarbonyl, $C_1$-$C_6$-thioalkyl, $C_1$-$C_6$-alkylsulfinyl, $C_1$-$C_6$-alkylsulfonyl, aminosulfonyl, $C_1$-$C_6$-alkylaminosulfonyl, di-$C_1$-$C_6$-alkylaminosulfonyl, phenyl, a C-linked 5-6 membered heteroaryl group, a $C_4$-$C_6$ carbocyclic group or a C-linked 5-6 membered heterocyclyl group, where said phenyl or cyclic groups may be optionally substituted by one or more hydroxyl, cyano, nitro, $C_1$-$C_6$-alkyl, $C_1$-$C_6$-alkenyl, $C_1$-$C_6$-alkynyl, $C_1$-$C_6$-alkoxy, $C_1$-$C_6$-alkenyloxy, $C_1$-$C_6$-alkynyloxy, halogen, $C_1$-$C_6$-alkylcarbonyl, carboxy, $C_1$-$C_6$-alkoxycarbonyl, amino, $C_1$-$C_6$-alkylamino, di-$C_1$-$C_6$-alkylamino, $C_1$-$C_6$-alkylaminocarbonyl, di-$C_1$-$C_6$-alkylaminocarbonyl, $C_1$-$C_6$-alkylcarbonylamino, $C_1$-$C_6$-alkylcarbonyl($C_1$-$C_6$-alkyl)amino, $C_1$-$C_6$-alkylsulfonylamino, $C_1$-$C_6$-alkylsulfonyl($C_1$-$C_6$-alkyl)amino, $C_1$-$C_6$-thioalkyl, $C_1$-$C_6$-alkylsulfinyl, $C_1$-$C_6$-alkylsulfonyl, aminosulfonyl, $C_1$-$C_6$-alkylaminosulfonyl or di-$C_1$-$C_6$-alkylaminosulfonyl groups, where each of the afore-mentioned hydrocarbon groups may be optionally substituted by one or more halogen, hydroxyl, $C_1$-$C_6$-alkoxy, amino, $C_1$-$C_6$-alkylamino, di-$C_1$-$C_6$-alkylamino or cyano; and $R^{21}$ represents hydroxyl, $C_1$-$C_4$-alkoxy, $C_2$-$C_4$-alkenyloxy, $C_2$-$C_4$-alkynyloxy, amino, $C_1$-$C_6$-alkylamino, di-$C_1$-$C_6$-alkylamino, $C_1$-$C_6$-alkylaminocarbonyl, di-$C_1$-$C_6$-alkylaminocarbonyl, $C_1$-$C_6$-alkylcarbonylamino, $C_1$-$C_6$-alkylcarbonyl($C_1$-$C_6$-alkyl)amino, $C_1$-$C_6$-alkylsulfonylamino, $C_1$-$C_6$-alkylsulfonyl($C_1$-$C_6$-alkyl)amino, an N-linked 5-6 membered heteroaryl group or an N-linked 5-6 membered heterocyclyl where said cyclic groups may be optionally substituted by one or more hydroxyl, nitro, $C_1$-$C_6$-alkyl, $C_1$-$C_6$-alkenyl, $C_1$-$C_6$-alkynyl, $C_1$-$C_6$-alkoxy, $C_1$-$C_6$-alkenyloxy, $C_1$-$C_6$-alkynyloxy, halogen, $C_1$-$C_6$-alkylcarbonyl, carboxy, $C_1$-$C_6$-alkoxycarbonyl, amino, $C_1$-$C_6$-alkylamino, di-$C_1$-$C_6$-alkylamino, $C_1$-$C_6$-alkylaminocarbonyl, di-$C_1$-$C_6$-alkylaminocarbonyl, $C_1$-$C_6$-alkylcarbonylamino, $C_1$-$C_6$-alkylcarbonyl($C_1$-$C_6$-alkyl)amino, $C_1$-$C_6$-alkylsulfonylamino, $C_1$-$C_6$-alkylsulfonyl($C_1$-$C_6$-alkyl)amino, $C_1$-$C_6$-thioalkyl, $C_1$-$C_6$-alkylsulfinyl, $C_1$-$C_6$-alkylsulfonyl, aminosulfonyl, $C_1$-$C_6$-alkylaminosulfonyl or di-$C_1$-$C_6$-alkylaminosulfonyl groups, where each of the afore-mentioned hydrocarbon groups may be optionally substituted by one or more halogen, hydroxyl, $C_1$-$C_6$-alkoxy, amino, $C_1$-$C_6$-alkylamino, di-$C_1$-$C_6$-alkylamino or cyano.

2. The compound according to claim 1, wherein $R^3$ is hydrogen or methyl.

3. The compound according to claim 1, wherein E is CH.

4. The compound according to claim 1, wherein $R^5$ is $SO_2NR^7R^8$, $R^7$ is hydrogen or methyl and $R^8$ is $C_1$-$C_6$-alkyl, $C_1$-$C_6$-alkoxy-$C_1$-$C_6$-alkyl, hydroxy$C_1$-$C_6$-alkyl, cyano$C_1$-$C_6$-alkyl, $NR^{18}R^{19}$—$C_1$-$C_6$-alkyl, phenyl, 5-6 membered heteroaryl, $C_4$-$C_8$-carbocyclyl, 5-8 membered heterocyclyl, phenyl fused to a $C_4$-$C_8$-carbocyclyl or a 5-8 membered heterocyclyl, benzyl or 5-8 membered heterocyclyl, where said rings may be substituted by one or more groups independently selected from hydroxyl, cyano, $C_1$-$C_6$-alkyl, $C_1$-$C_6$-alkoxy, halogen, $C_1$-$C_6$-alkylcarbonyl, amino, $C_1$-$C_6$-alkylamino, di-$C_1$-$C_6$-alkylamino, $C_1$-$C_6$-alkylaminocarbonyl, di-$C_1$-$C_6$-alkylaminocarbonyl, $C_1$-$C_6$-alkylcarbonylamino, $C_1$-$C_6$-alkylcarbonyl($C_1$-$C_6$-alkyl)amino or 5-6 membered heteroaryl, where each of the afore-mentioned hydrocarbon groups may be optionally substituted by one or more halogen, hydroxyl and $C_1$-$C_6$-alkoxy.

5. The compound according to claim 4, wherein $R^8$ is phenyl, optionally substituted by one or more cyano, trifluoromethyl, $C_1$-$C_6$-alkyl or halo.

6. The compound according to claim 1 where $R^6$ is halo, $C_1$-$C_3$-alkyl or $C_1$-$C_3$-alkoxy.

7. A pharmaceutical composition, comprising:
the compound according to claim 1 and
a suitable excipient.

8. A method of treating respiratory diseases, comprising:
administering an effective amount the compound according to claim 1 to a subject in need thereof.

9. The method according to claim 8, wherein the respiratory disease is asthma.

\* \* \* \* \*